US007388009B2

(12) United States Patent
Leftheris et al.

(10) Patent No.: US 7,388,009 B2
(45) Date of Patent: Jun. 17, 2008

(54) HETEROARYL-SUBSTITUTED PYRROLO-TRIAZINE COMPOUNDS USEFUL AS KINASE INHIBITORS

(75) Inventors: Katerina Leftheris, Skillman, NJ (US); Stephen T. Wrobleski, Whitehouse Station, NJ (US); Alaric J. Dyckman, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 413 days.

(21) Appl. No.: 10/678,388

(22) Filed: Oct. 3, 2003

(65) Prior Publication Data
US 2005/0043306 A1 Feb. 24, 2005

Related U.S. Application Data

(63) Continuation-in-part of application No. 10/420,399, filed on Apr. 22, 2003.

(60) Provisional application No. 60/374,938, filed on Apr. 23, 2002.

(51) Int. Cl.
*C07D 487/04* (2006.01)
*C07D 403/08* (2006.01)
*C07D 403/14* (2006.01)
*A61K 31/53* (2006.01)
*A61P 9/10* (2006.01)
*A61P 19/02* (2006.01)
*A61P 19/04* (2006.01)
*A61P 11/00* (2006.01)
*A61P 17/06* (2006.01)
*A61P 35/00* (2006.01)

(52) U.S. Cl. ...................................... 514/243; 544/183
(58) Field of Classification Search ................. 544/183; 514/243
See application file for complete search history.

(56) References Cited

U.S. PATENT DOCUMENTS

| 6,147,080 | A | 11/2000 | Bemis et al. |
| 6,277,989 | B1 | 8/2001 | Chakravarty et al. |
| 2003/0069244 | A1 | 4/2003 | Leftheris et al. |
| 2003/0186983 | A1 | 10/2003 | Mastalerz et al. |

FOREIGN PATENT DOCUMENTS

| WO | WO 00/56738 | 9/2000 |
| WO | WO 00/71129 | 11/2000 |
| WO | WO 01/14378 | 3/2001 |
| WO | WO 01/27089 | 4/2001 |
| WO | WO 01/34605 | 5/2001 |
| WO | WO 02/40486 A2 | 5/2002 |
| WO | WO 03/091229 | 6/2003 |
| WO | WO 2004/043912 | 5/2004 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
West, Anthony R., Solid State Chemistry and its Applications, Wiley, New York, 1988, pp. 358 & 365.*
Rankin et al., Br. J. Rheumatol. vol. 34, 334-342, 1995.*
Moreland et al., Ann Intern. Med., vol. 130, 478-486, 1999.*
Henry et al., Drugs. Fut., vol. 24, pp. 1345-1354 (1999).
U.S. Appl. No. 10/623,171, filed Jul. 18, 2003, Bhide et al.
U.S. Appl. No. 10/633,997, filed Aug. 4, 2003, Bhide et al.
Branger, J., et al., "Anti-Inflammatory Effects of a p38 Mitogen-Activated Protein Kinase Inhibitor During Human Endotoxemia", The Journal of Immunology, vol. 168, pp. 4070-4077, (2002).
Davis, J. C., Jr., "Understanding the Role of Tumor Necrosis Factor Inhibition in Ankylosing Spondylitis", Seminars in Arthritis and Rheumatism, vol. 34, pp. 668-677, (2004).
Gottlieb, A. B., et al., TNF Inhibition Rapidly Down-Regulates Multiple Proinflammatory Pathways in Psoriasis Plaques[1], The Journal of Immunology, vol. 175, pp. 2721-2729, (2005).
Hideshima, T. et al, "Targeting p38 MAPK Inhibits multiple myeloma cell growth in the bone marrow milleu", Blood, vol. 101(2), pp. 703-706, (2003).
Johansen, C., et al., "Protein Expression of TNF-α in Psoriatic Skin Is Regulated at a Posttrancriptional Level by MAPK-Activated Protein Kinase 2[1]", The Journal of Immunology, vol. 176, pp. 1431-1438, (2006).
Johansen, C., et al., "The mitogen-activated protein kinases p38 and KRK1/2 are increased in lesional psoriatic skin", British Journal of Dermatology, vol. 152, pp. 37-42, (2005).
Kumar, S., et al., "P38 MAP Kinaes: Key Signalling Molecules as Therapeutic Targets for Inflammatory Diseases", vol. 2, pp. 717-726, (2003).

(Continued)

*Primary Examiner*—Venkataraman Balasubramanian
(74) *Attorney, Agent, or Firm*—Anastasia P. Winslow; Joseph C. Wang

(57) ABSTRACT

Compounds having the formula (I),

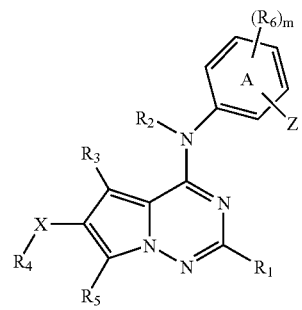

and pharmaceutically acceptable salts, prodrugs, and solvates thereof, are useful as kinase inhibitors, wherein $R_1$, $R_2$, $R_3$, $R_4$, $R_5$, $R_6$, X and Z are as described in the specification.

20 Claims, No Drawings

OTHER PUBLICATIONS

Mease, P. J. et al., "Psoriatic arthritis treatment: biological response modifiers", Ann. Rheum. Dis., vol. 64 (Suppl. II), pp. ii78-ii82, (2005).

Navas, TA, et al., Inhibition of p38α MAPK enhances proteasome inhibitor-induced apoptosis of myeloma cells by modulating Hsp27, Bcl-$X_L$, MCl-1 and p53 levels in vitro and inhibits tumor growth in vivo, Leukemia, 1-11 (2006).

Papp, K. A., "The long-term efficacy and safety of new biological therapies for psoriasis", Arch. Dermatol. Res. vol. 298, pp. 7-15, (2006).

Saklatvala, J., "The p38 MAP kinase pathway as a therapeutic target in inflammatory disease", Current Opinion in Pharmacology, vol. 4, pp. 372-377, (2004).

Waetzig G. H., "p38 Mitogen-Activated Protein Kinase Is Activated and Linked to TNF-α Signaling in Inflammatory Bowel Disease[1]", The Journal of Immunology, vol. 168, pp. 5342-5351, (2002).

* cited by examiner

HETEROARYL-SUBSTITUTED PYRROLO-TRIAZINE COMPOUNDS USEFUL AS KINASE INHIBITORS

RELATED APPLICATIONS

This application is a continuation-in-part application of U.S. patent application Ser. No. 10/420,399, filed Apr. 22, 2003, now pending, which claims the benefit of U.S. Provisional Application Ser. No. 60/374,938, filed Apr. 23, 2002. The entire contents of each of said applications is incorporated herein by reference.

FIELD OF THE INVENTION

This invention relates to pyrrolotriazine compounds, more particularly, to heteroaryl-substituted pyrrolotriazine aniline compounds useful for treating p38 kinase-associated conditions. The invention further pertains to pharmaceutical compositions containing at least one compound according to the invention useful for treating p38 kinase-associated conditions and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345-1354 (1999); Salituro et al., *Curr. Med. Chem.*, 6:807-823 (1999)]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, 34:334-342 (1995)], and soluble TNF-α receptor-Fc fusion protein (Etanercept) [Moreland et al., *Ann. Intern. Med.*, 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945, 418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G. D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides certain pyrrolotriazine compounds, particularly, pyrrolotriazine aniline compounds useful as kinase inhibitors, particularly kinases p38α and β. Pyrrolotriazine compounds useful as tyrosine kinase inhibitors are disclosed in U.S. patent application Ser. No. 09/573, 829, filed May 18, 2000, assigned to the present assignee. Methods of treating p38 kinase-associated conditions as well as pyrrolotriazine compounds useful for that purpose are described in U.S. patent application Ser. No. 10/036,293, assigned to the present assignee and having common inventors herewith, which claims the benefit of U.S. Provisional Application No. 60/249,877, filed Nov. 17, 2000, and U.S. Provisional Application No. 60/310,561, filed Aug. 7, 2001. Methods of making pyrrolotriazine compounds are described in U.S. patent application Ser. No. 10/289,101, filed Nov. 6, 2002. Pyrrolotriazine compounds substituted with an acidic group reportedly having sPLA$_2$-inhibitory activity are disclosed in WO 01/14378 A1 to Shionogi & Co., Ltd, published Mar. 1, 2001 in Japanese. Each of the patent applications, patents, and publications referred to herein is incorporated herein by reference.

SUMMARY OF THE INVENTION

The instant invention pertains to compounds of formula (I),

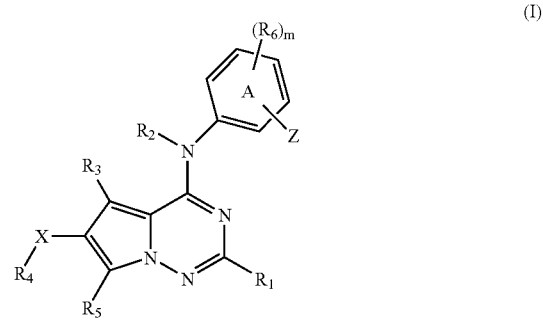

(I)

its enantiomers, diastereomers, and pharmaceutically-acceptable salts, prodrugs, and solvates thereof, wherein:

X is selected from —O—, —OC(=O)—, —S—, —S(=O)—, —SO$_2$—, —C(=O)—, —CO$_2$—, —NR$_8$—, —NR$_8$C(=O)—, —NR$_8$C(=O)NR$_9$—, —NR$_8$CO$_2$—, —NR$_8$SO$_2$—, —NR$_8$SO$_2$NR$_9$—, —SO$_2$NR$_8$—, —C(=O)NR$_8$—, halogen, nitro, and cyano, or X is absent;

Z is optionally-substituted heteroaryl;

R$_1$ and R$_5$ are independently selected from hydrogen, alkyl, substituted alkyl, —OR$_{14}$, —SR$_{14}$, —OC(=O)R$_{14}$, —CO$_2$R$_{14}$, —C(=O)NR$_{14}$R$_{14a}$, —NR$_{14}$R$_{14a}$, —S(=O)R$_{14}$, —SO$_2$R$_{14}$, —SO$_2$NR$_{14}$R$_{14a}$, —NR$_{14}$SO$_2$NR$_{14a}$R$_{14b}$, —NR$_{14a}$SO$_2$R$_{14}$, —NR$_{14}$C(=O)R$_{14a}$, —NR$_{14}$CO$_2$R$_{14a}$, —NR$_{14}$C(=O)NR$_{14a}$R$_{14b}$, halogen, nitro, and cyano;

R$_2$ is hydrogen or C$_{1-4}$alkyl;

R$_3$ is hydrogen, methyl, perfluoromethyl, methoxy, halogen, cyano, NH$_2$, or NH(CH$_3$);

$R_4$ is selected from:
 a) hydrogen, provided that $R_4$ is not hydrogen if X is —S(=O)—, —SO$_2$—, —NR$_8$CO$_2$—, or —NR$_8$SO$_2$—;
 b) alkyl, alkenyl, and alkynyl optionally independently substituted with keto and/or one to four $R_{17}$;
 c) aryl and heteroaryl either of which may be optionally independently substituted with one to three $R_{16}$; and
 d) heterocyclo and cycloalkyl either of which may be optionally independently substituted with keto and/or one to three $R_{16}$; or
 e) $R_4$ is absent if X is halogen, nitro, or cyano;

$R_6$ is attached to any available carbon atom of phenyl ring A and at each occurrence is independently selected from alkyl, halogen, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, phenyl, benzyl, aryloxy, and benzyloxy, wherein each $R_6$ group in turn may be further substituted by one to two $R_{18}$;

$R_8$, $R_9$, $R_{14}$, $R_{14a}$ and $R_{14b}$ are independently selected from hydrogen, alkyl, substituted alkyl, aryl, cycloalkyl, heterocyclo, and heteroaryl, except when $R_{14}$ is joined to a sulphonyl group as in —S(=O)R$_{14}$, —SO$_2$R$_{14}$, and —NR$_{14a}$SO$_2$R$_{14}$, then $R_{14}$ is not hydrogen;

$R_{16}$ is selected from alkyl, $R_{17}$, and $C_{1-4}$alkyl substituted with keto (=O) and/or one to three $R_{17}$;

$R_{17}$ is selected from
 (a) halogen, haloalkyl, haloalkoxy, nitro, cyano, —SR$_{23}$, —OR$_{23}$, —NR$_{23}$R$_{24}$, —NR$_{23}$SO$_2$R$_{25}$, —SO$_2$R$_{25}$, —SO$_2$NR$_{23}$R$_{24}$, —CO$_2$R$_{23}$, —C(=O)R$_{23}$, —C(=O)NR$_{23}$R$_{24}$, —OC(=O)R$_{23}$, —OC(=O)NR$_{23}$R$_{24}$, —NR$_{23}$C(=O)R$_{24}$, —NR$_{23}$CO$_2$R$_{24}$;
 (b) aryl or heteroaryl either of which may be optionally substituted with one to three $R_{26}$; or
 (c) cycloalkyl or heterocyclo optionally substituted with keto(=O) and/or one to three $R_{26}$;

$R_{18}$ and $R_{26}$ are independently selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, $C_{1-4}$alkoxy, $C_{1-4}$alkylthio, phenyl, five to six membered heterocyclo, (phenyl)$C_{1-4}$alkyl, phenoxy, and (phenyl)$C_{1-4}$alkoxy;

$R_{23}$ and $R_{24}$ are each independently selected from hydrogen, alkyl, alkenyl, substituted alkyl, substituted alkenyl, aryl, cycloalkyl, heteroaryl, and heterocyclo;

$R_{25}$ is selected from alkyl, substituted alkyl, aryl, heteroaryl, cycloalkyl and heterocyclo; and m is 0, 1, 2 or 3.

The invention further pertains to pharmaceutical compositions containing compounds of formula (I), and to methods of treating conditions associated with the activity of p38 kinase (α and β), comprising administering to a mammal a pharmaceutically-acceptable amount of a compound of formula (I).

DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 12 carbon atoms, preferably 1 to 6 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms.

The term "substituted alkyl" refers to an alkyl group substituted by one to four substituents selected from halogen, hydroxy, alkoxy, keto (=O), alkanoyl, aryloxy, alkanoyloxy, NR$_a$R$_b$, alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, —SO$_2$NR$_a$R$_b$, nitro, cyano, —CO$_2$H, —CONR$_a$R$_b$, alkoxycarbonyl, aryl, guanidino and heteroaryls or heterocyclos (such as indolyl, imidazolyl, furyl, thienyl, thiazolyl, pyrrolidyl, pyridyl, pyrimidyl and the like), wherein $R_a$ and $R_b$ are selected from hydrogen, alkyl, aryl, aralkyl, cycloalkyl, cycloalkylalkyl, heteroaryl, heteroarylalkyl, heterocycle, and heterocyclealkyl. The substituent on the alkyl optionally in turn may be further substituted, in which case it will be with substituted one or more of $C_{1-4}$alkyl, $C_{2-4}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenyloxy, and/or benzyloxy.

The term "alkenyl" refers to straight or branched chain hydrocarbon groups of 2 to 20 carbon atoms, preferably 2 to 15 carbon atoms, and most preferably 2 to 8 carbon atoms, having at least one double bond, and depending on the number of carbon atoms, up to four double bonds.

The term "substituted alkenyl" refers to an alkenyl group substituted by one to two substituents selected from those recited above for substituted alkyl groups.

The term "alkynyl" refers to straight or branched chain hydrocarbon groups of 2 to 20 carbon atoms, preferably 2 to 15 carbon atoms, and most preferably 2 to 8 carbon atoms, having at least one triple bond, and depending on the number of carbon atoms, up to four triple bonds.

The term "substituted alkynyl" refers to an alkynyl group substituted by one to two substituents selected from those recited above for alkyl groups.

When the term alkyl is used in connection with another group, as in heterocycloalkyl or cycloalkylalkyl, this means the identified (first named) group is bonded directly through an alkyl group which may be branched or straight chain (e.g., cyclopropyl$C_{1-4}$alkyl means a cyclopropyl group bonded through a straight or branched chain alkyl group having one to four carbon atoms.). In the case of substituents, as in "substituted cycloalkylalkyl," the alkyl portion of the group, besides being branched or straight chain, may be substituted as recited above for substituted alkyl groups and/or the first named group (e.g., cycloalkyl) may be substituted as recited herein for that group.

The term "halogen" or "halo" refers to fluorine, chlorine, bromine and iodine.

The term "aryl" refers to monocyclic or bicyclic aromatic substituted or unsubstituted hydrocarbon groups having 6 to 12 carbon atoms in the ring portion, such as phenyl, naphthyl, and biphenyl groups. Aryl groups may optionally include one to three additional rings (either cycloalkyl, heterocyclo or heteroaryl) fused thereto. Examples include:

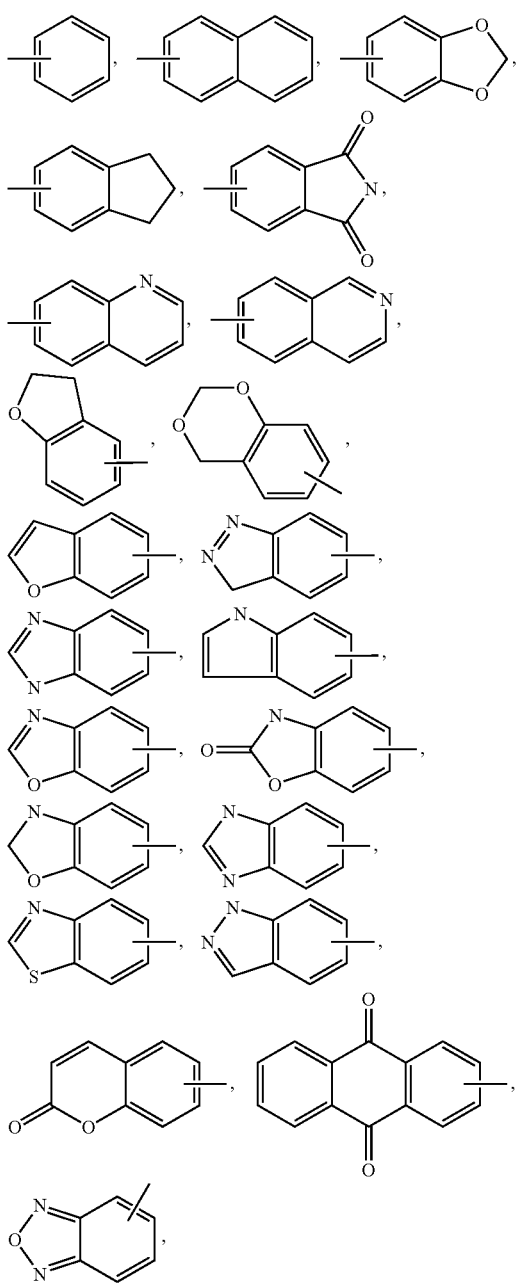

and the like. Each ring of the aryl may be optionally substituted with one to three $R_c$ groups, wherein $R_c$ at each occurrence is selected from alkyl, substituted alkyl, halogen, trifluoromethoxy, trifluoromethyl, —SR, —OR, —NRR', —NRSO$_2$R', —SO$_2$R, —SO$_2$NRR', —CO$_2$R', —C(=O)R', —C(=O)NRR', —OC(=O)R', —OC(=O)NRR', —NRC(=O)R', —NRCO$_2$R', phenyl, $C_{3-7}$ cycloalkyl, and five-to-six membered heterocyclo or heteroaryl, wherein each R and R' is selected from hydrogen, alkyl, substituted alkyl, alkenyl, substituted alkenyl, phenyl, $C_{3-7}$cycloalkyl, and five-to-six membered heterocyclo or heteroaryl, except in the case of a sulfonyl group, then R is not going to be hydrogen. Each substituent $R_c$ optionally in turn may be further substituted by one or more (preferably 0 to 2) $R_d$ groups, wherein $R_d$ is selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenylethyl, phenyloxy, and benzyloxy.

The term "aralkyl" refers to an aryl group bonded directly through an alkyl group, such as benzyl, wherein the alkyl group may be branched or straight chain. In the case of a "substituted aralkyl," the alkyl portion of the group besides being branched or straight chain, may be substituted as recited above for substituted alkyl groups and/or the aryl portion may be substituted as recited herein for aryl. Thus, the term "optionally substituted benzyl" refers to the group

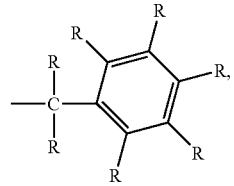

wherein each R group may be hydrogen or may also be selected from $R_c$ as defined above, in turn optionally substituted with one or more $R_d$. At least two of these "R" groups should be hydrogen and preferably at least five of the "R" groups is hydrogen. A preferred benzyl group involves the alkyl-portion being branched to define

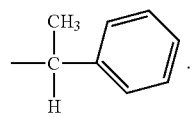

The term "heteroaryl" refers to a substituted or unsubstituted aromatic group for example, which is a 4 to 7 membered monocyclic, 7 to 11 membered bicyclic, or 10 to 15 membered tricyclic ring system, which has at least one heteroatom and at least one carbon atom-containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. It may optionally be substituted as valance allows with one to three (preferably 0 to 2) $R_c$ groups, as defined above for aryl, which in turn may be substituted with one or more (preferably 0 to 2) $R_d$ groups, also as recited above. Additionally, a heteroaryl group may be an aromatic, heterocyclic group as defined above wherein one or two carbon atoms of the ring, as valence allows, is replaced with a carbonyl group, wherein the heteroaryl ring then may be partially unsaturated with the carbonyl group imparting aromaticity to the ring, e.g., as in a group 2,4-dihydro-[1,2,4]triazol-3-one.

Exemplary monocyclic heteroaryl groups include pyrrolyl, pyrazolyl, pyrazolinyl, imidazolyl, oxazolyl, isoxazolyl, thiazolyl (i.e., 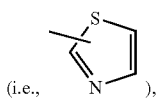), thiadiazolyl, isothiazolyl, furanyl, thienyl, oxadiazolyl, pyridyl, pyrazinyl, pyrimidinyl, pyridazinyl, triazinyl and the like. Additionally, heteroaryl groups include groups such as 2,4-dihydro-[1,2,4]triazol-3-one (i.e., 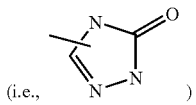)

and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "cycloalkyl" refers to a saturated or partially unsaturated non-aromatic cyclic hydrocarbon ring system, preferably containing 1 to 3 rings and 3 to 7 carbon atoms per ring, which may be substituted or unsubstituted and/or which may be fused with a $C_3$-$C_7$ carbocyclic ring, a heterocyclic ring, or which may have a bridge of 3 to 4 carbon atoms. The cycloalkyl groups including any available carbon or nitrogen atoms on any fused or bridged rings optionally may have 0 to 3 (preferably 0-2) substituents selected from $R_c$ groups, as recited above, and/or from keto (where appropriate) which in turn may be substituted with one to three $R_d$ groups, also as recited above. Thus, when it is stated that a carbon-carbon bridge may be optionally substituted, it is meant that the carbon atoms in the bridged ring optionally may be substituted with an $R_c$ group, which preferably is seleted from $C_{1-4}$alkyl, $C_{2-4}$alkenyl, halogen, haloalkyl, haloalkoxy, cyano, amino, $C_{1-4}$alkylamino, amino$C_{1-4}$alkyl, hydroxy, hydroxy$C_{1-4}$alkyl, and $C_{1-4}$alkoxy. Exemplary cycloalkyl groups include cyclopropyl, cyclobutyl, cyclopentyl, cyclohexyl, cycloheptyl, bicycloheptane, cycloctyl, cyclodecyl, cyclododecyl, and adamantyl.

The terms "heterocycle", "heterocyclic" and "heterocyclo" each refer to a fully saturated or partially unsaturated nonaromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quaternized. Preferably two adjacent heteroatoms are not simultaneously selected from oxygen and nitrogen. The heterocyclic group may be attached at any nitrogen or carbon atom. The heterocyclo groups optionally may have 0 to 3 (preferably 0-2) substituents selected from keto (═O), and/or one or more $R_c$ groups, as recited above, which in turn may be substituted with one to three $R_d$ groups, also as recited above.

Exemplary monocyclic heterocyclic groups include pyrrolidinyl, tetrahydrofuryl, piperidinyl, piperazinyl, tetrahydropyranyl, morpholinyl, thiamorpholinyl, and the like.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., oxadiazolyl), the reference is intended to include rings having, as valence allows, 0 to 3, preferably 0-2, substituents, selected from those recited above for the aryl, cycloalkyl, heterocyclo and/or heteroaryl groups, as appropriate. Thus, for example, an "optionally-substituted oxadiazolyl" means an oxadiazolyl ring that is unsubstituted or substituted with one group selected from the $R_c$ groups, as defined above for aryl, which in turn may be substituted with one or more (preferably 0 to 2) $R_d$ groups, also as recited above.

Additionally, when reference is made to a specific heteroaryl or heterocyclo group, the reference is intended to include those systems having the maximum number of non-cumulative double bonds or less than the maximum number of double bonds. Thus, for example, the term "isoquinoline" refers to isoquinoline and tetrahydroisoquinoline.

Additionally, it should be understood that one skilled in the field may make appropriate selections for the substituents for the aryl, cycloalkyl, heterocyclo, and heteroaryl groups to provide stable compounds and compounds useful as pharmaceutically-acceptable compounds and/or intermediate compounds useful in making pharmaceutically-acceptable compounds. Thus, for example, in compounds of formula (I), when Z is a cyclopropyl ring, preferably the ring has no more than two substituents, and preferably said substituents do not comprise nitro ($NO_2$), more than one cyano group, or three halogen groups. Similarly, when m is 3, preferably $R_6$, the substituents on the phenyl ring A, are not all nitro, and so forth.

The term "heteroatoms" shall include oxygen, sulfur and nitrogen.

The term "haloalkyl" means an alkyl having one or more halo substituents.

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, aryl, cycloalkyl, and so forth, are as follows: alkoxy is —$OR^e$, alkanoyl is —$C(═O)R^e$, aryloxy is —OAr, alkanoyloxy is —$OC(═O)R^e$, amino is —$NH_2$, alkylamino is —$NHR^e$ or —$N(R^e)_2$, arylamino is —NHAr or —$NR^eAr$, aralkylamino is —NH—$R^f$—Ar, alkanoylamino is —NH—$C(═O)R^e$, aroylamino is —NH—$C(═O)Ar$, aralkanoylamino is —NH—$C(═O)R_f$—Ar, thiol is —SH, alkylthio is —$SR^e$, arylthio is —SAr, aralkylthio is —S—$R^f$—Ar, alkylthiono is —S(=O)R$^e$, arylthiono is —S(=O)Ar, aralkylthiono is —S(=O)R$^f$—Ar, alkylsulfonyl is —SO$_{(q)}$R$^e$, arylsulfonyl is —SO$_{(q)}$Ar, arylsulfonylamine is —NHSO$_{(q)}$Ar, alkylsulfonylamine is —NHSO$_2$R$^e$, aralkylsulfonyl is —SO$_{(q)}$R$^f$Ar, sulfonamido is —SO$_2$NH$_2$, substituted sulfonamide is —SO$_2$NHR$^e$ or —SO$_2$N(R$^e$)$_2$, nitro is —NO$_2$, carboxy is —CO$_2$H, carbamyl is —CONH$_2$, substituted carbamyl is —C(=O)NHR$^g$ or —C(=O)NR$^g$R$^h$, alkoxycarbonyl is —C(=O)OR$^e$, carboxyalkyl is —R$^f$—CO$_2$H, , sulfonic acid is —SO$_3$H, arylsulfonylamine is —NHSO$_{(q)}$Ar, guanidino is

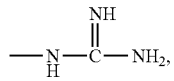

and ureido is

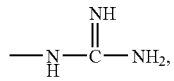

wherein R$^e$ is alkyl or substituted alkyl as defined above, R$^f$ is alkylene or substituted alkylene as defined above, R$^g$ and R$^h$ are selected from alkyl, substituted alkyl, aryl, aralkyl, cycloalkyl, heterocyclo, and heteraryl; Ar is an aryl as defined above, and q is 2 or 3.

In compounds of formula (I), when reference is made to numbering of the positions on the A (phenyl) and Z rings wherein Z is oxadiazol-2-yl, the numbering shall be intended to be as follows:

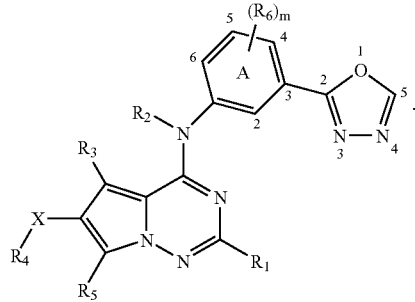

Thus, for example, when reference is made to compounds of formula (I) wherein the group Z is oxadiazol-2-yl substituted at the 5 position with a group R$_{7a}$, this is intended to refer to compounds having the formula,

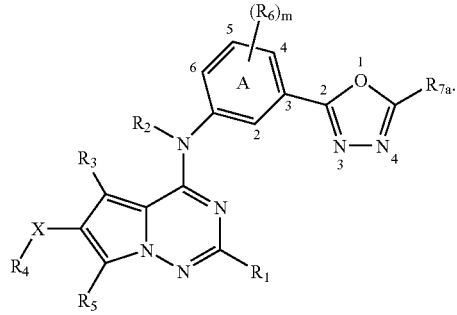

Likewise, as a further example, when reference is made to compounds of formula (I) wherein the group R$_6$, is optionally attached to the phenyl ring A at the 4 and/or 6 positions, this is intended to refer to compounds having the formula,

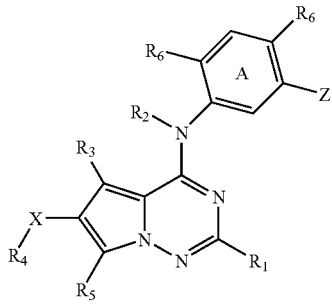

wherein the R$_6$ groups are optionally present.

Likewise, when reference is made to compounds of formula I wherein the group Z is triazol-5-yl, the numbering of the triazolyl is intended as follows:

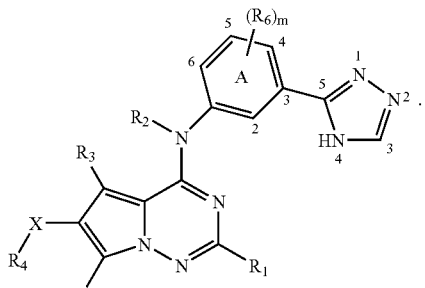

Thus, when it is stated that Z is a 2,4-dihydro-[1,2,4]triazol-5-yl-3-one, this is intended to refer to a "Z" ring as follows:

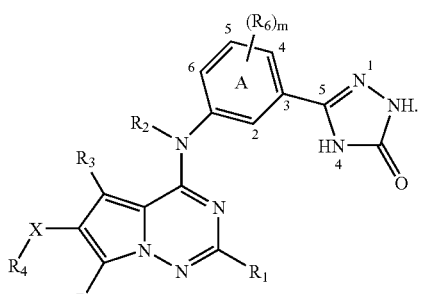

Throughout the specification, groups and substituents thereof may be chosen by one skilled in the field to provide stable moieties and compounds.

The compounds of the present invention may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of the present invention may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds of the present invention may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the present invention may also have prodrug forms. Any compound that will be converted in vivo to provide the bioactive agent (i.e., the compound for formula (I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992), each of which is incorporated herein by reference.

It should further be understood that solvates (e.g., hydrates) of the compounds of Formula (I) are also with the scope of the present invention. Methods of solvation are generally known in the art.

Preferred Compounds

Preferred compounds include those having the structure of formula (I*),

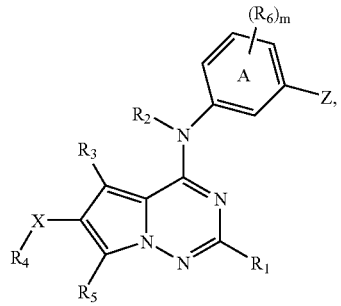

(I*)

enantiomers, diastereomers, salts and solvates thereof, wherein:

X is selected from —O—, —OC(=O)—, —S—, —S(=O)—, —SO$_2$—, —C(=O)—, —CO$_2$—, —NR$_8$—, —NR$_8$C(=O)—, —NR$_8$C(=O)NR$_9$—, —NR$_8$CO$_2$—, —NR$_8$SO$_2$—, —NR$_8$SO$_2$NR$_9$—, —SO$_2$NR$_8$—, —C(=O)NR$_8$—, halogen, nitro, and cyano, or X is absent;

Z is an optionally-substituted five membered heteroaryl;

$R_1$ and $R_5$ are independently selected from hydrogen, alkyl, and substituted alkyl;

$R_2$ is hydrogen or $C_{1-4}$alkyl;

$R_3$ is hydrogen, methyl, perfluoromethyl, methoxy, halogen, cyano, $NH_2$, or $NH(CH_3)$;

$R_4$ is selected from:

(a) hydrogen, provided that $R_4$ is not hydrogen if X is —S(=O)—, —SO$_2$—, —NR$_8$CO$_2$—, or —NR$_8$SO$_2$—;

(b) alkyl, alkenyl, and alkynyl optionally substituted with keto and/or one to four $R_{17}$;

(c) aryl and heteroaryl optionally substituted with one to three $R_{16}$; and (d) heterocyclo and cycloalkyl optionally substituted with keto and/or one to three $R_{16}$; or (e) $R_4$ is absent if X is halogen, nitro, or cyano;

$R_6$ is attached to any available carbon atom of phenyl ring A and at each occurrence is independently selected from alkyl, halogen, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, phenyl, benzyl, aryloxy, and benzyloxy;

$R_8$ and $R_9$ are independently selected from hydrogen, alkyl, and substituted alkyl;

$R_{16}$ is selected from alkyl, $R_{17}$, and $C_{1-4}$alkyl substituted with keto (=O) and/or one to three $R_{17}$;

$R_{17}$ is selected from halogen, haloalkyl, haloalkoxy, nitro, cyano, —SR$_{23}$, —OR$_{23}$, —NR$_{23}$R$_{24}$, —NR$_{23}$SO$_2$R$_{25}$, —SO$_2$R$_{25}$, —SO$_2$NR$_{23}$R$_{24}$, —CO$_2$R$_{23}$, —C(=O)R$_{23}$, —C(=O)NR$_{23}$R$_{24}$, —OC(=O)R$_{23}$, —OC(=O) NR$_{23}$R$_{24}$, —NR$_{23}$C(=O)R$_{24}$, —NR$_{23}$CO$_2$R$_{24}$, aryl or heteroaryl optionally substituted with one to three $R_{26}$; or cycloalkyl or heterocyclo optionally substituted with keto (=O) and/or one to three $R_{26}$;

$R_{23}$ and $R_{24}$ are each independently selected from hydrogen, alkyl, and substituted alkyl;

$R_{25}$ is selected from alkyl and substituted alkyl;

$R_{26}$ is independently selected from $C_{1-6}$alkyl, $C_{2-6}$alkenyl, halogen, haloC$_{1-4}$alkyl, haloC$_{1-4}$alkoxy, cyano, nitro, amino, $C_{1-4}$alkylamino, aminoC$_{1-4}$alkyl, hydroxy, hydroxyC$_{1-4}$alkyl, $C_{1-4}$alkoxy, $C_{1-4}$alkylthio, phenyl, benzyl, phenyloxy, and benzyloxy; and m is 0, 1, or 2.

Further preferred compounds are those having formula (I*), above, and pharmaceutically-acceptable salts, prodrugs, and solvates thereof, wherein:

$R_1$ and $R_5$ are independently selected from hydrogen, alkyl, and substituted alkyl;

$R_2$ is hydrogen or $C_{1-4}$alkyl;

$R_3$ is methyl, —CF$_3$, or —OCF$_3$;

X is —C(=O)—, —NR$_8$C(=O)—, or —C(=O)NR$_8$—, wherein $R_8$ is hydrogen or $C_{1-4}$alkyl;

Z is a heteroaryl selected from one of:

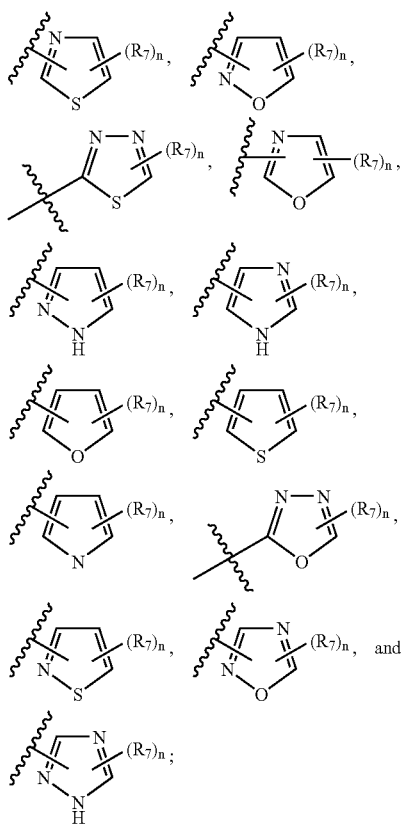

wherein n can be 0, 1, or 2; and $R_7$ is selected from $C_{1-4}$alkyl, substituted $C_{1-4}$alkyl, trifluoromethyl, trifluoromethoxy, halogen, cyano, amino, —NH($C_{1-4}$alkyl), N($C_{1-4}$alkyl)$_2$, hydroxy, $C_{1-4}$alkoxy, thiol, alkylthio, phenyl, benzyl, phenyloxy, benzyloxy, $C_{3-7}$cycloalkyl, five-membered heteroaryl, and five to six membered heterocyclo; or as valence permits, $R_7$ may be taken together with one of two bonds forming a double bond of ring Z to form a keto (=O) group, or two $R_7$ groups attached to adjacent carbon atoms or an adjacent carbon and nitrogen atom may join to form a fused heterocyclo or carbocyclic ring, said fused ring in turn being optionally substituted with one to two of $C_{1-4}$alkyl, trifluoromethyl, trifluoromethoxy, halogen, cyano, amino, $C_{1-4}$alkylalmino, hydroxy, $C_{1-4}$alkoxy, phenyl, benzyl, phenyloxy, and benzyloxy;

$R_4$ is hydrogen, $C_{2-6}$alkyl, $C_{1-4}$alkyl optionally substituted with one to three $R_{17}$, aryl or heteroaryl optionally substituted with one to three $R_{16}$, or cycloalkyl or heterocycle optionally-substituted with keto (=O) and/or one to three $R_{16}$;

$R_6$ is attached to the phenyl ring A at the 4 and/or 6 positions and is selected from $C_{1-6}$alkyl, substituted $C_{1-4}$alkyl, halogen, cyano, trifluoromethoxy, trifluoromethyl, —OR$_{27}$, —C(=O)alkyl, —OC(=O)alkyl, —NR$_{27}$R$_{28}$, —SR$_{27}$, —NO$_2$, —CO$_2$R$_{27}$, —CONH$_2$, —SO$_3$H, —S(=O)alkyl, —S(=O)aryl, —NHSO$_2$-aryl-R$_{27}$, —SO$_2$NHR$_{27}$, —CONHR$_{27}$, and —NHC(=O)NHR$_{27}$;

$R_{16}$ is selected from $C_{1-4}$alkyl, $R_{17}$, and $C_{1-4}$alkyl substituted with keto and/or one to two $R_{17}$;

$R_{17}$ is selected from halogen, hydroxy, $C_{1-4}$alkoxy, trifluoromethyl, trifluoromethoxy, cyano, nitro, phenyl, benzyl, phenyloxy, benzyloxy, NH$_2$, NH($C_{1-4}$alkyl), N($C_{1-4alkyl)2}$, $C_{3-7}$cycloalkyl, and five or six membered heteroaryl or heterocycle;

$R_{27}$ and $R_{28}$ are selected from hydrogen and $C_{1-4}$alkyl; and m is 1 or 2.

More preferred are compounds having the formula (I*), as recited above, wherein:

$R_1$ and $R_5$ are both hydrogen;

$R_2$ is hydrogen or $C_{1-4}$alkyl;

$R_3$ is methyl, —CF$_3$, or —OCF$_3$;

X is —C(=O)—, —C(=O)NH— or —C(=O)N($C_{1-4}$alkyl)-;

Z is a 1,3,4-oxadiazol-2-yl optionally substituted at the 5 position with $R_7$; or a group selected from one of

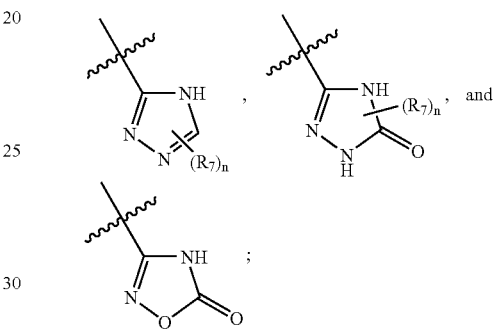

wherein $R_7$ is lower alkyl, and n is 0 or 1;

$R_4$ is hydrogen, $C_{2-6}$alkyl, $C_{1-4}$alkyl optionally substituted with one to three $R_{17}$, aryl or heteroaryl optionally substituted with one to three $R_{16}$, or cycloalkyl or heterocycle optionally-substituted with keto (=O), and/or one to three $R_{16}$;

$R_6$ is attached to the phenyl ring A at the 4 and/or 6 positions and is selected from hydrogen, $C_{1-4}$alkyl, halogen, trifluoromethoxy, trifluoromethyl, hydroxy, $C_{1-4}$alkoxy, cyano, NH$_2$, NH($C_{1-4}$alkyl), and N($C_{1-4}$alkyl)$_2$;

$R_{16}$ is selected from $C_{1-4}$alkyl, $R_{17}$, and $C_{1-4}$alkyl substituted with keto and/or one to two $R_{17}$;

$R_{17}$ is selected from halogen, hydroxy, $C_{1-4}$alkoxy, trifluoromethyl, trifluoromethoxy, cyano, nitro, phenyl, benzyl, phenyloxy, benzyloxy, NH$_2$, NH($C_{1-4}$alkyl), N($C_{1-4}$alkyl)$_2$, cyclopentyl, cyclohexyl, or five or six membered heteroaryl or heterocycle; and m is 1 or 2.

In compounds of formula (I*), preferably $R_3$ is methyl, —CF$_3$, or —OCF$_3$, more preferably methyl; X preferably is —C(=O)— or —C(=O)NH—; and Z is preferably 5-methyl-1,3,4-oxadiazol-2-yl,

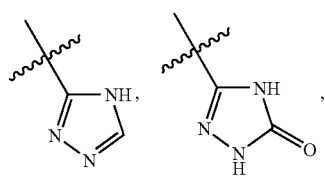

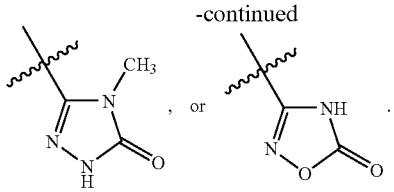

Preferably when X is —C(=O)NH—, $R_4$ is $C_{2-6}$alkyl or substituted $C_{1-4}$alkyl, more preferably $C_{1-4}$alkyl or optionally-substituted benzyl. When X is —C(=O)—, preferably $R_4$ is an optionally-substituted aryl or heteroaryl.

When $R_4$ is a heterocyclo, advantageously it is selected from diazepinyl, morpholinyl, piperidinyl, and pyrrolidinyl, said heterocycle being optionally substituted with one to two of $C_{1-4}$alkyl, hydroxy, $C_{1-4}$alkoxy, phenyl, and/or benzyl. When X is —C(=O)— and $R_4$ is aryl or heteroaryl, preferably $R_4$ is phenyl, pyridinyl, pyrimidinyl, or pyrazinyl, optionally-substituted with $C_{1-4}$alkyl, halogen, hydroxy, $C_{1-4}$alkoxy, trifluoromethyl, trifluoromethoxy, cyano, nitro, phenyl, benzyl, phenyloxy, benzyloxy, $NH_2$, $NH(C_{1-4}$alkyl), $N(C_{1-4}$alkyl$)_2$, cyclopentyl, cyclohexyl, or five or six membered heteroaryl or heterocycle.

In compounds of formula (I) and (I*), preferably phenyl ring A is unsubstituted or has one substituent. Said optional substituent $R_6$ is preferably attached at the 6 position and is selected from $C_{1-4}$alkyl, halogen, trifluoromethoxy, trifluoromethyl, hydroxy, $C_{1-4}$alkoxy, nitro, and cyano, more preferably the substituent $R_6$ is methyl or ethyl attached at the 6 position, para to Z in formula (I*).

Further preferred are compounds of formula (I*), referenced above, and pharmaceutically acceptable salts, prodrugs, and solvates thereof, wherein:

$R_1$, $R_2$ and $R_5$ are each hydrogen;
$R_3$ is methyl;
Z is 1,3,4-oxadiazol-2-yl optionally substituted at the 5 position with methyl or ethyl, or is one of

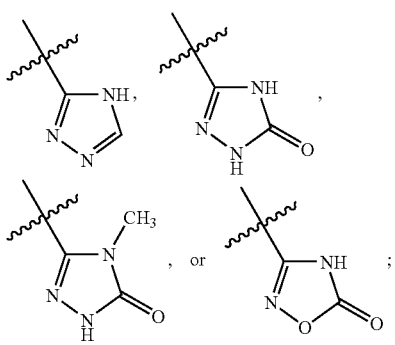

X is —C(=O)— or —C(=O)—NH— (attached to the pyrrolo-triazine via the carbonyl), wherein, when X is —C(=O)—, then $R_4$ is phenyl or pyridyl optionally substituted with up to two $R_{16}$; and when X is —C(=O)NH—, $R_4$ is straight or branched $C_{2-6}$alkyl or optionally-substituted benzyl;

$R_6$ is attached to phenyl ring A at the 6 position and is methyl, ethyl, halogen, trifluoromethoxy, trifluoromethyl, hydroxy, methoxy, ethoxy, or cyano;

$R_{16}$ is selected from $C_{1-4}$alkyl, trifluoromethyl, trifluoromethoxy, halogen, cyano, nitro, amino, $C_{1-4}$alkylamino, amino$C_{1-4}$alkyl, hydroxy, hydroxy$C_{1-4}$alkyl, halo$C_{1-4}$alkyl, $C_{1-4}$alkoxy, phenyl, benzyl, phenyloxy, and benzyloxy; and m is 1.

Most preferred are compounds as immediately defined above, wherein $R_1$, $R_2$ and $R_5$ are each hydrogen;
$R_3$ is methyl;
Z is 1,3,4-oxadiazol-2-yl optionally substituted at the 5 position with methyl, or is

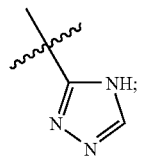

X is —C(=O)— or —C(=O)—NH— (attached to the pyrrolo-triazine via the carbonyl), wherein, when X is —C(=O)—, then $R_4$ is phenyl or pyridyl optionally substituted with up to two $R_{16}$; and when X is —C(=O)NH—, $R_4$ is straight or branched $C_{2-6}$alkyl or optionally-substituted benzyl;

$R_6$ is attached to phenyl ring A at the 6 position and is lower alkyl;

$R_6$ is selected from $C_{1-4}$alkyl, trifluoromethyl, trifluoromethoxy, halogen, cyano, nitro, amino, $C_{1-4}$alkylamino, amino$C_{1-4}$alkyl, hydroxy, hydroxy$C_{1-4}$alkyl, halo$C_{1-4}$alkyl, and $C_{1-4}$alkoxy; and m is 1.

Utility

The compounds of the invention are selective inhibitors of p38 kinase activity, and in particular, isoforms p38α and p38β. Accordingly, compounds of formula (I) have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. When reference is made herein to inhibition of "p-38α/β kinase," this means that either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

In view of their activity as inhibitors of p-38α/β kinase, compounds of Formula (I) are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

The present invention thus provides methods for treating such conditions, comprising administering to a subject in need thereof an effective amount of at least one compound of Formula (I) or a salt thereof. The methods of treating p38 kinase-associated conditions may comprise administering compounds of Formula (I) alone or in combination with each other and/or other suitable therapeutic agents useful in treating such conditions. Exemplary of such other therapeutic agents include corticosteroids, rolipram, calphostin, CSAIDs, 4-substituted imidazo [1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrastemal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of formula (I), including the compounds described in the examples hereof, have been tested in one or more of the assays described below and have shown activity as inhibitors of p38α/β enzymes and TNF-α.

Biological Assays

Generation of P38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247-1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5 \times 10^6$/ml in assay medium (RPMI medium containing 10% fetal bovine serum). 50 ul of cell suspension was incubated with 50 ul of test compound (4× concentration in assay medium containing 0.2% DMSO) in 96-well tissue culture plates for 5 minutes at RT. 100 ul of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60μ prepared from three 20μ additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 μl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 μM; $[\gamma-^{33}P]ATP$, 3 nM,; MBP (Sigma, #M1891), 2 μg/well; p38, 10 nM; and DMSO, 0.3%.

TNF-α Production by LPS-Stimulated Mice

Mice (Balb/c female, 6-8 weeks of age, Harlan Labs; n=8/treatment group) were injected intraperitoneally with 50 ug/kg lipopolysaccharide (LPS; *E coli* strain 0111:B4, Sigma) suspended in sterile saline. Ninety minutes later, mice were sedated by $CO_2:O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

Abbreviations

For ease of reference, the following abbreviations are employed herein, including the methods of preparation and Examples that follow:

Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate Boc=tert-butyloxycarbonyl
DCM=dichloromethane
DCE=1,2-dichloroethane
DMF=dimethyl formamide
DMSO=dimethyl sulfoxide
TEA=triethylamine
TFA=trifluoroacetic acid
THF=tetrahydrofuran
HATU=O-(7-Azabenzotriazol-1-yl-N,N,N',N'-tetramethyluronim hexafluorophosphate
$POCl_3$=phosphorous oxychloride
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaOH=sodium hydroxide
Pd=palladium
Pd/C=palladium on carbon
min=minute(s)
L=liter
mL=milliliter
μL=microliter
g=gram(s)
mg=milligram(s)
mol=moles
mmol=millimole(s)
meq=milliequivalent
RT or rt.=room temperature
ret. t.=HPLC retention time (minutes)
sat or sat'd=saturated
aq.=aqueous
TLC=thin layer chromatography
HPLC=high performance liquid chromatography
RP HPLC=reverse phase HPLC
LC/MS=high performance liquid chromatography/mass spectrometry
MS=mass spectrometry
NMR=nuclear magnetic resonance
mp=melting point Methods of Preparation Compounds of formula I may generally be prepared according to the following schemes and the knowledge of one skilled in the art, and/or the methods described in U.S. patent applications Ser. Nos. 10/036,293, 09/573,829, and/or 10/420,399, incorporated herein by reference.

Scheme 1

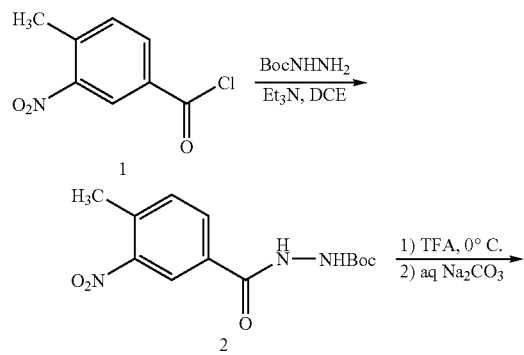

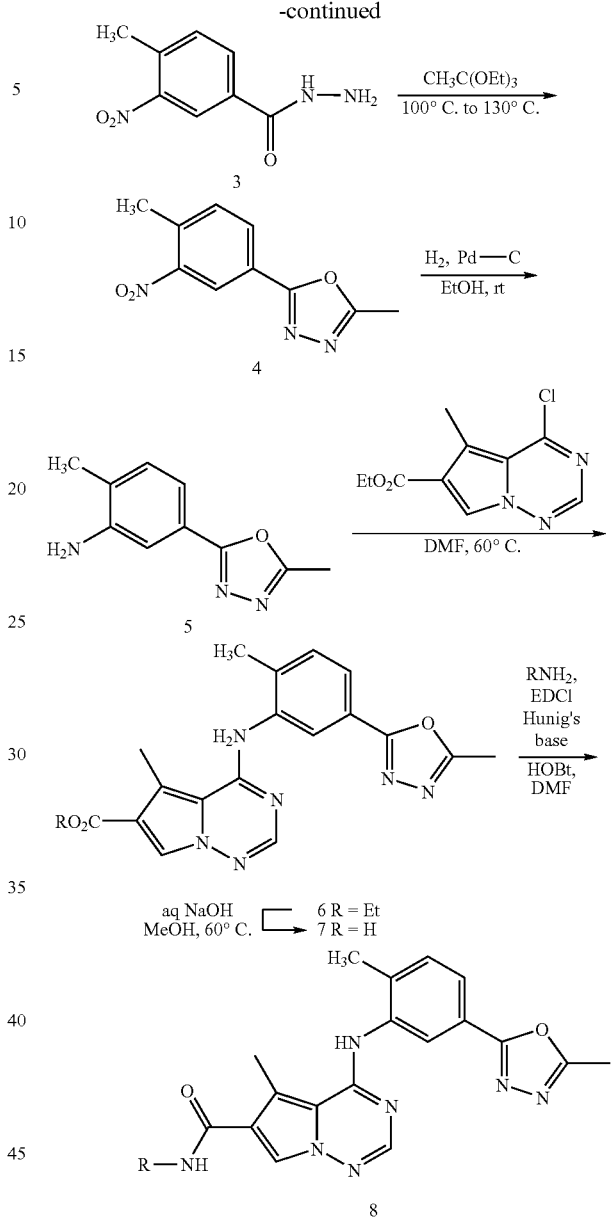

Compound (8) can be prepared from commercially-available compound (1) as depicted in Scheme 1. Compound (1) can be reacted with tert-butyl carbazate in an organic solvent, such as DCE, in the presence of a base, such as TEA, to afford compound (2). Compound (2) can reacted with an acid, such as TFA, and neutralized with a base, such as aqueous sodium carbonate, to afford compound (3). Formation of the oxadiazole can be accomplished by heating compound (3) in triethyl orthoacetate to afford compound (4) that can then be reduced with hydrogen in the presence of a suitable catalyst, such as Pd/C, in a solvent, such as EtOH, to afford compound (5). Compound (5) can then be coupled to the chloropyrrolotriazine in a solvent such as DMF to provide compound (6). Hydrolysis of compound (6) in the presence of aqueous NaOH in a suitable solvent, such as MeOH, affords compound (7) which can be reacted with an amine $RNH_2$ in the presence of coupling reagents, such as EDCI and HOBt, and an organic base, such as diisopropylethylamine, in an organic solvent, such as DMF, to afford compound (8). The chloropyrrolotriazine can be prepared as shown in Scheme 2.

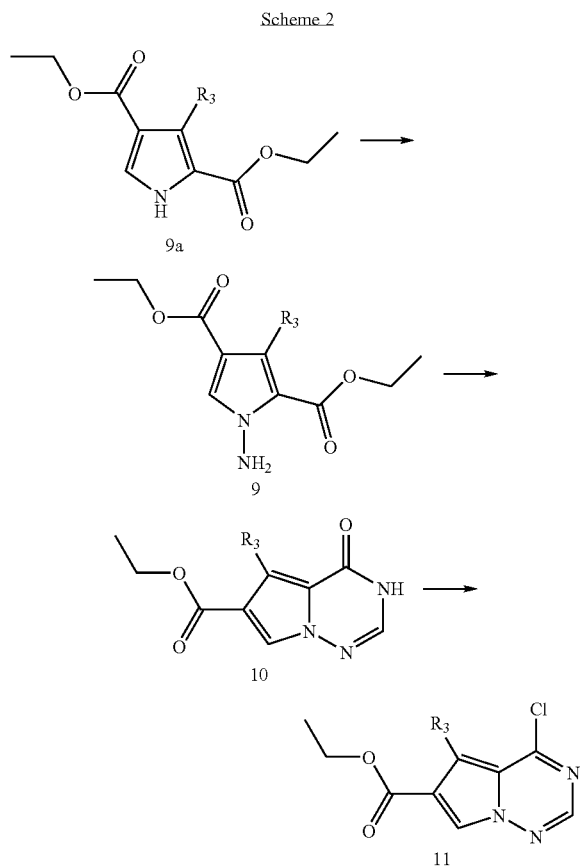

3-methyl-1-pyrrole-2,4-diethyl ester (9a) can be reacted with chloramine in ether (such as diethyl ether or MTBE) to produce compound (9). Advantageously, about 2.0 equiv. of KOtBu can be used with 1.2-1.4 equiv. of chloramine in MTBE to produce compound (9). Reacting compound (9) in formamide with acetic acid produces compound (10). Compound (10) can be reacted with DIPEA and POCl₃ in toluene to produce chloropyrrolotriazine compound (11). Methods for producing the chloropyrrolotriazine can also be found in U.S. patent application Ser. Nos. 10/036,293, 09/573,829, 10/289,010, and/or 10/420,399, incorporated herein by reference.

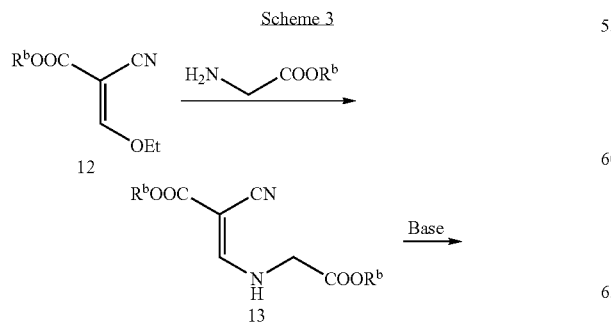

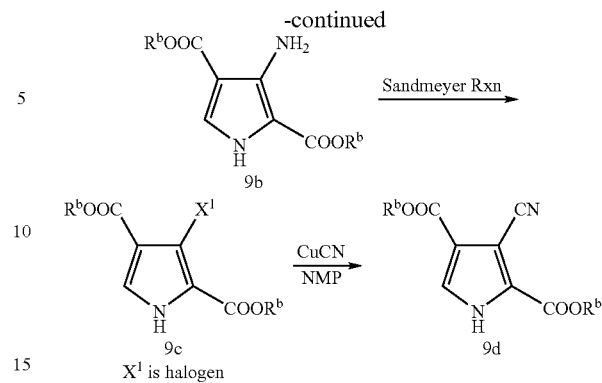

Scheme 3 shows methods for making compounds (9a) (see scheme 2), wherein R₃ is amino (9b), halogen (9c), or cyano (9d). Glycine ethyl ester (12) can be added to an alkyl alkoxy methylene cyanoacetate at from rt to 80° C. to obtain compound (13). Compound (13) is cyclized to form pyrrole (9b) upon treatment with a strong base, such as lithium hexamethyldisilazane, at from −78° C. to rt in an organic solvent such as THF. Pyrrole (9b) can be converted to a halide using sodium nitrite in an organic solvent, such as DMF, and a halide source, such as CuBr to yield compound (9c). Compound (9c) can be converted to compound (9d) using CuCN in an organic solvent such as NMP at elevated temperatures. Alternatively, compound (9b) can be directly converted to compound (9d) using sodium nitrite in an organic solvent, such as DMF, and a cyanide source such as CuCN. Compounds (9a)-(9d) can be used as described in previous schemes (e.g., Scheme 1), to form compounds of Formula (I) herein.

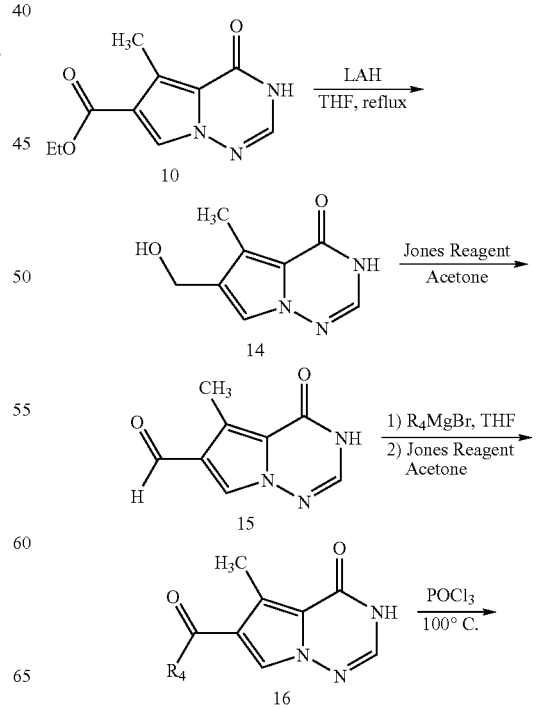

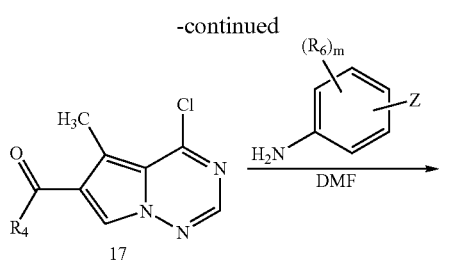

Reduction of the ester group of pyrrolotriazine 10 (see Scheme 2) with a suitable reducing agent such as LAH in an aprotic organic solvent such as THF produces the alcohol (14). Alcohol (14) is oxidized to the aldehyde (15) with a suitable oxidant, such as Jones Reagent. Aldehyde (15) is reacted with a suitable organometallic reagent (such as phenylmagnesium bromide) to afford an intermediate secondary alcohol product that is subsequently oxidized to ketone (16) with a suitable oxidant, such as Jones Reagent. A chlorinating agent, such as $POCl_3$, is used to convert (16) to chloride (17). Chloride (17) is reacted with an aniline having the desired heteroaryl substituent Z, in a suitable solvent, such as DMF, at rt or elevated temperature to provide product (18), a compound of formula (I).

In addition, other compounds of formula I may be prepared using procedures generally known to those skilled in the art. In particular, the following examples provide additional methods for the preparation of the compounds of this invention.

The invention will now be further described by the following working examples, which are preferred embodiments of the invention. HPLC purifications were done on C18 reverse phase (RP) columns using water MeOH mixtures and TFA as buffer solution. These examples are illustrative rather than limiting. There may be other embodiments that fall within the spirit and scope of the invention as defined by the appended claims.

For the following examples, HPLC retention times were determined using a YMC S5 ODS 4.6 mm×50 mm Ballistic chromatography column with a 4 minute total gradient elution time and a flow rate of 4 mL/minute. The elution gradient uses 100% of solvent A and gradually increases to 100% of solvent B over the 4 min elution time (solvent A=10% MeOH/90% water/0.2% phosphoric acid and solvent B=90% MeOH/10% water/0.2% phosphoric acid). Eluted products were detected using a uv detector at a wavelength of 220 nm.

EXAMPLE 1

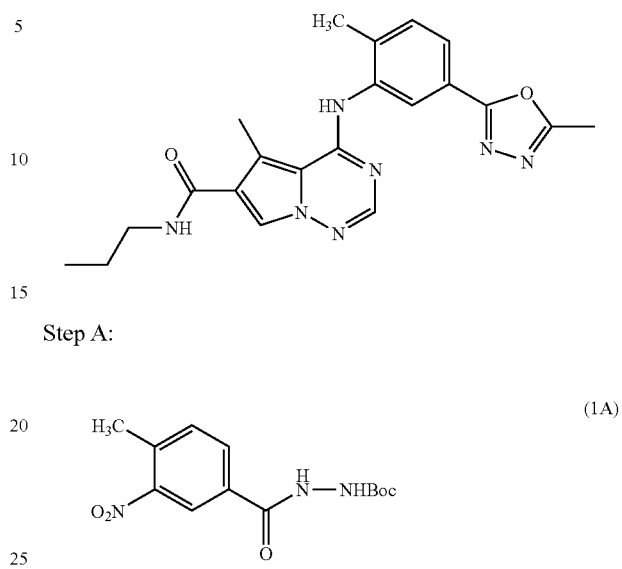

Step A:

(1A)

To a rt solution of tert-butyl carbazate (2.6 g, 20 mmol) and TEA (3.1 mL, 22 mmol) in DCE (100 mL) was added a solution of 4-methyl-3-nitrobenzoyl chloride in DCE (25 mL) over 30 minutes. After the addition was complete, the resulting cloudy mixture was stirred at rt for 2 h, then the mixture was successively washed with 10% aqueous citric acid (2×75 mL) and brine (100 mL), then dried over anhydrous sodium sulfate. The solution was diluted with EtOAc (100 mL), filtered, and concentrated in vacuo to a volume of approximately 50 mL. The mixture was diluted with hexanes (50 mL) and sonicated for a few minutes and the resulting precipitated solid was collected by vacuum filtration and dried in vacuo to afford 4.7 g (74%) of compound 1A as a white solid. HPLC $t_R$=2.54 min. $^1$H NMR (400 MHz, $d_6$-DMSO): δ 10.30 (s, 1H), 8.86 (s, 1H), 8.27 (s, 1H), 7.91 (d, 1H), 7.48 (d, 1H), 2.41 (s, 3H), 1.26 (s, 9H).

Step B:

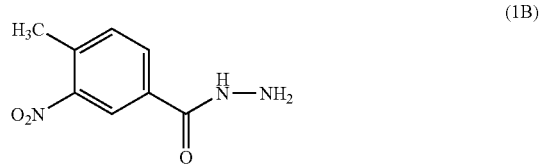

(1B)

Compound 1A (4.4 g, 15 mmol) as a solid was added in portions to trifluoroacetic acid (45 mL) at 0° C., and the mixture was stirred at this temperature for 30 min and at rt for an additional 30 minutes. The mixture was then concentrated in vacuo and the resulting white solid was partitioned between 2N aq sodium carbonate (200 mL) and EtOAc (200 mL). The layers were separated and the aqueous portion was extracted with additional EtOAc (5×100 mL), and the combined extracts were washed with brine (100 mL), dried over anhydrous sodium sulfate, filtered, and concentrated in vacuo to yield 2.96 g (99%) of compound 1B as a white solid. HPLC $t_R$=1.05 min. $^1$H NMR (500 MHz, $d_6$-DMSO): δ 10.20 (br s, 1H), 8.42 (s, 1H), 8.05 (d, 1H), 7.62 (d, 1H), 5.43 (br s, 2H), 2.56 (s, 3H). LCMS [M+H]$^+$=196.3.

Step C:

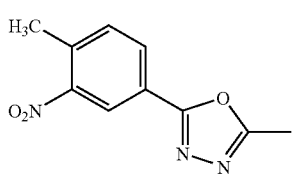
(1C)

A suspension of compound 1B (2.9 g, 15 mmol) in triethyl orthoacetate (50 mL) was heated to 100° C. giving a clear solution. After heating at this temperature for 2 h, the mixture was heated to 130° C. for an additional hour then cooled to rt and heterogeneously concentrated in vacuo. The resulting residue was dissolved in EtOAc (250 mL), then washed with water (100 mL) and brine (75 mL), then dried over anhydrous sodium sulfate, filtered, and concentrated in vacuo to afford 3.2 g of compound 1C as a light yellow solid. HPLC $t_R$=2.45 min. $^1$H NMR (500 MHz, CDCl$_3$): δ 8.57 (s, 1H), 8.16 (d, 1H), 7.49 (d, 1H), 2.66 (s, 3H), 2.63 (s, 3H).

Step D:

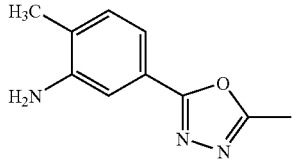
(1D)

To a suspension of compound 4 (0.37 g) in EtOH (40 mL) was added 5% Pd/C (35 mg), and the mixture was allowed to stir under an atmosphere of hydrogen at rt for 2h. The mixture was filtered through Celite and the resulting clear filtrate was concentrated in vacuo and the residue was triturated with MeOH. Filtration and drying of the collected solid afforded 220 mg of compound 5 as an off-white solid. HPLC $t_R$=1.19 min. $^1$H NMR (500 MHz, $d_6$-DMSO): δ 7.23 (s, 1H), 7.08 (d, 1H), 7.05 (d, 1H), 5.22 (s, 2H), 2.53 (s, 3H), 2.10 (s, 3H). LCMS [M+H]$^+$=190.3.

Step E:

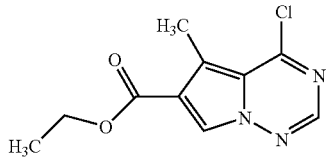
(1E)

To a suspension of the starting oxopyrrolotriazine (3.00 g, 13.6 mmol) in toluene (45 mL) was added dropwise phosphorus oxychloride (1.90 mL, 20.4 mmol) and N,N-DIPEA (2.37 mL, 13.6 mmol) successively at rt. The resulting mixture was heated at reflux for 36 h, allowed to cool to rt, and then poured into an ice-cold mixture of sat'd sodium bicarbonate solution (150 mL) and toluene (60 mL). The organic layer was separated and the aqueous layer extracted with toluene (3×50 mL). The combined extract was washed with sat'd sodium bicarbonate solution and brine and dried over anhydrous MgSO$_4$. Evaporation of solvent in vacuo afforded compound 1E (3.26 g, 100% yield) as a yellow solid.

Step F:

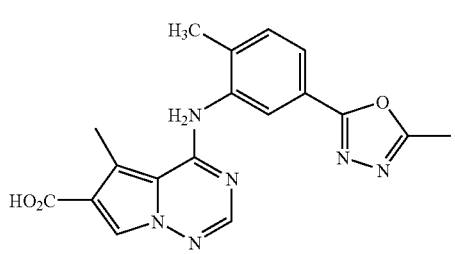
(1F)

A mixture of compound 1D (0.28 g, 1.48 mmol) and the chloropyrrolotriazine 1E from step E (0.32 g, 1.33 mmol) in 6 mL of DMF was heated at 60° C. for 24 h then cooled to rt and diluted with water (10 mL). After stirring at rt for 30 min, the solid was collected by filtration and dried in vacuo to afford 430 mg (74%) of compound 1F as an off-white solid. HPLC $t_R$=3.21 min. LCMS [M+H]$^+$=393.2.

Step G:

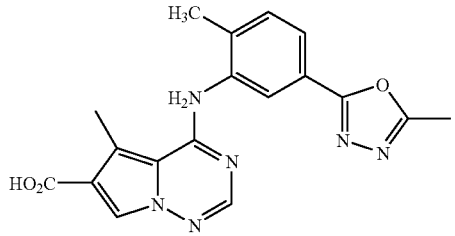
(1G)

To a slurry of compound 1F (0.41 g, 1.04 mmol) in MeOH at rt was added 3N aqueous NaOH solution (3 mL) and the resulting mixture was heated to 50° C. for 1.5 h and then at 60° C. for an additional 4 h. The mixture was cooled to rt and concentrated in vacuo and the residue was dissolved in water (5 mL). The solution was acidified to a pH of 2 by slowly adding 1 N aqueous HCl. After stirring for 15 min, the resulting precipitated solid was collected by filtration and washed with additional water (2×10 mL), then dried in vacuo to afford 0.38 g of compound 1G as an off-white solid.

HPLC $t_R$=2.55 min. LCMS [M+H]$^+$=365.4.

Step H,

EXAMPLE 1

A solution of compound 1G (50 mg, 0.14 mmol), EDCI (34 mg, 0.18 mmol), HOBt (22 mg, 0.16 mmol), and DIPEA (0.026 mL, 0.15 mmol) in DMF (0.3 mL) was stirred at rt for 1 h. To this solution was then added n-propylamine (0.034 mL, 0.41 mmol), and the mixture was stirred at rt for an additional hour. Water (0.1 mL) was added and the solution was stirred for 5 min, followed by addition of 10% aqueous sodium carbonate solution (1 mL). The resulting precipitated solid was collected by filtration, washed with water (5 mL), and dried in vacuo to afford 37 mg of Example 1 as an off-white solid. HPLC $t_R$=2.74 min. LCMS [M+H]$^+$=406.2.

EXAMPLES 2-6

The additional examples listed below in Table 1 were prepared from compound 8 as described above for Example 1, except in Step 8 the n-propylamine was replaced with the appropriate amine.

TABLE 1

| Ex. # | Compound Structure | HPLC and LCMS Data |
| --- | --- | --- |
| 2 | 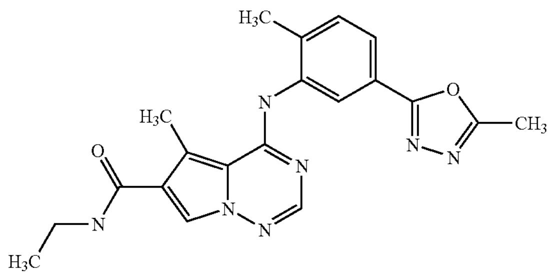 | HPLC $t_R$ = 2.46 min<br>LCMS [M + H]$^+$ = 392.2 |
| 3 | 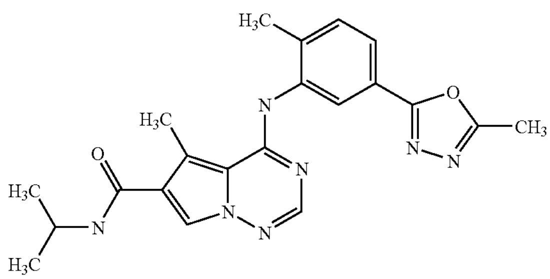 | HPLC $t_R$ = 2.66 min<br>LCMS [M + H]$^+$ = 406.2 |
| 4 | Chiral | HPLC $t_R$ = 2.87 min<br>LCMS [M + H]$^+$ = 420.2 |
| 5 | Chiral | HPLC $t_R$ = 2.87 min<br>LCMS [M + H]$^+$ = 420.2 |
| 6 | 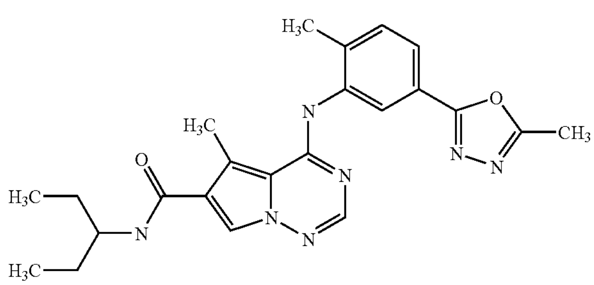 | HPLC $t_R$ = 3.06 min<br>LCMS [M + H]$^+$ = 434.2 |

EXAMPLES 7-24
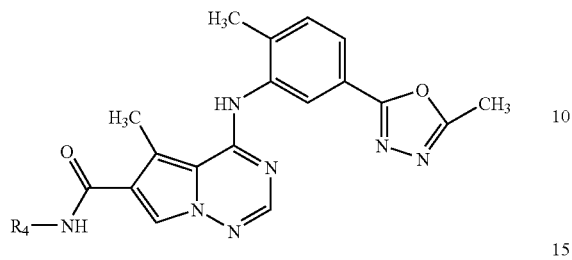
Compounds having the formula (Ia), above, wherein $R_4$ has the values listed in the following Table 2, can be prepared following the same procedure described for Example 1, using the appropriate amine in place of n-propylamine.

EXAMPLE 25

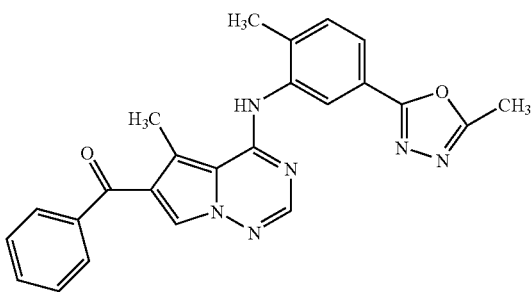

Step A:

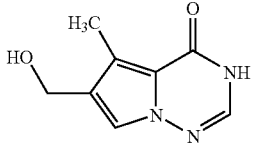
(25A)

To a solution of LAH (13.7 g, 362 mmol) in THF (800 mL) was added ester having the formula

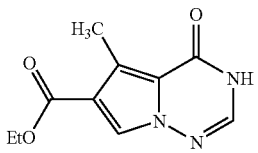

(8 g, 36.2 mmol) in several portions at rt. The reaction mixture was heated to reflux for 30 min., then cooled to rt, carefully quenched by being poured into ice water (1 L), and stirred rapidly for 1 h. The mixture was extracted with EtOAc and the combined extracts were washed with brine, dried over MgSO$_4$, filtered, and concentrated to give compound 25A (5.60 g, 86%).

Step B:

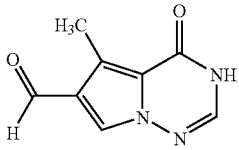
(25B)

To a suspension of compound 25A (1.0 g, 5.58 mmol) in acetone (80 mL) at 0° C. was added Jones Reagent (1.9 mL) dropwise. The reaction was stirred at 0° C. for 1 h, then carefully quenched with 2-propanol. Sat'd aq. sodium bicarbonate (100 mL) was added, and the mixture was extracted with EtOAc (5×100 mL). The combined extracts were washed with sat'd aq. sodium bicarbonate (1×100 mL), water (1×100 mL), and brine (1×100 mL), then dried over MgSO$_4$, filtered, and concentrated to afford compound 25B (647 mg, 65%). HPLC ret. t. (min): 1.50, MW: 177.16, LCMS[M+H]$^+$= 178.

Step C:

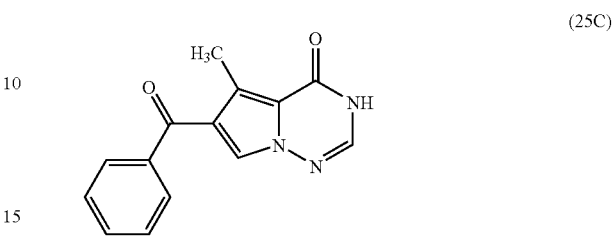
(25C)

To a solution of compound 25B (600 mg, 3.39 mmol) in THF (80 mL) at 0° C. was added phenylmagnesium bromide (3M, 2.94 mL, 8.8 mL) dropwise over 5 min. After stirring for 30 min at 0° C., the reaction was warmed to rt over 1 h and quenched with sat'd aq. ammonium chloride. The mixture was extracted with EtOAc and the extracts were dried, filtered, and concentrated to afford the benzylic alcohol intermediate. The crude benzylic alcohol was dissolved in acetone (50 mL) and cooled to 0° C. Jones Reagent (1 mL) was added dropwise and the reaction was stirred at 0° C. for 1 h, then carefully quenched with 2-propanol. Sat'd aq. sodium bicarbonate (50 mL) was added and the mixture was extracted with EtOAc (4×50 mL). The combined extracts were washed with sat'd aq. sodium bicarbonate (1×50 mL), water (1×50 mL), and brine (1×50 mL) before being dried over MgSO$_4$, filtered, and concentrated to afford compound 25C (563 mg, 66% over 2 steps). HPLC ret .t. (min): 2.82, MW: 253.26, LCMS[M+H]$^+$=254.

Step D:

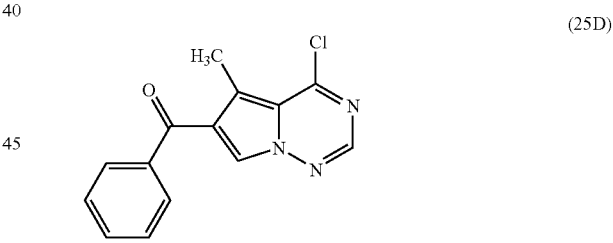
(25D)

Ketone 25C (152 mg, 0.6 mmol) was placed in POCl$_3$ (5 mL) and heated to 100° C. for 1.75 h. The reaction was cooled to rt and the excess POCl$_3$ was evaporated under vacuum. The residue was dissolved in anhydrous DCM (10 mL) and added dropwise to a rapidly stirred solution of sat'd aq. sodium bicarbonate (50 ml) and DCM (50 mL) at 0° C. The mixture was stirred for 1 h, then the aqueous phase was extracted with DCM (3×50 mL). The organic phases were washed with sat'd aq. sodium bicarbonate (1×50 mL), water (1×50 mL), and brine (1×50 mL), then dried over MgSO$_4$, filtered, and concentrated to afford the chloride 25D (163 mg, 100%).

Step E:

The compound of Example 25 can be prepared as described in Example 1, Step 6, by coupling the oxadiazolyl compound 5 of Example 1, Step 4, with the above chloropyrrolotriazine.

EXAMPLE 26

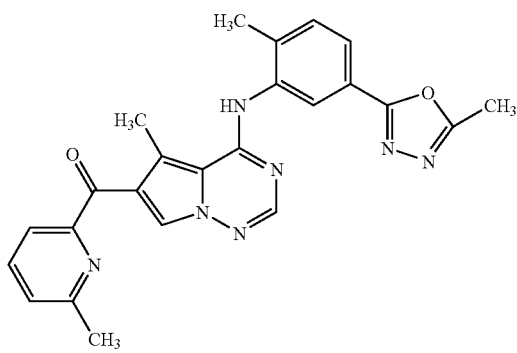

Step A:

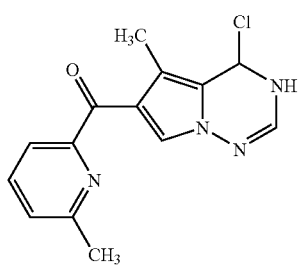

(26A)

To a solution of the compound 25B (160 mg, 0.90 mmol) in THF (10 mL) at 0° C. was added 6-methyl-2-pyridylmagnesium bromide (0.25M, 14.4 mL, 3.6 mM) dropwise over 5 min. After stirring for 30 min at 0° C., the reaction was warmed to rt and stirred for 16 h. Additional aliquots of 6-methyl-2-pyridylmagnesium bromide were added to complete the conversion of the starting material and the reaction was quenched with sat'd aq. ammonium chloride. The mixture was extracted with EtOAc and the extracts were dried, filtered, and concentrated to afford a reddish brown semisolid material. This material was dissolved in acetone (10 mL) and cooled to 0° C. Jones Reagent (0.4 mL) was added dropwise and the reaction was stirred at 0° C. for 1 h, then carefully quenched with 2-propanol. Sat'd aq. sodium bicarbonate (15 mL) was added and the mixture was extracted with EtOAc (4×20 mL). The combined extracts were washed with sat'd aq. sodium bicarbonate (1×20 mL), water (1×20 mL), and brine (1×20 mL), then dried over MgSO4, filtered, and concentrated to afford compound 26A (145 mg, 60% over 2 steps).

Step B:

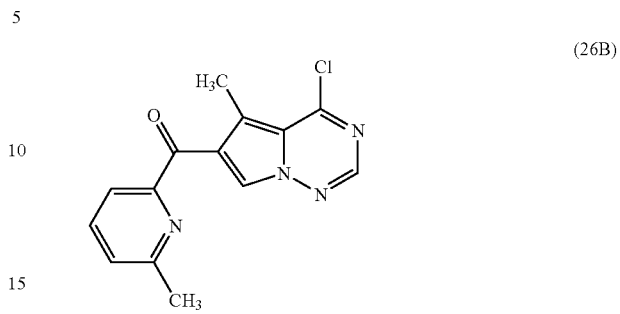

(26B)

Ketone 26A (75 mg, 0.28 mmol) was placed in POCl3 (4 mL) and heated to 100° C. overnight. The reaction was cooled to rt and the excess POCl3 was evaporated under vacuum. The residue was dissolved in anhydrous DCM (10 mL) and added dropwise to a rapidly stirred solution of sat'd aq. sodium bicarbonate (50 ml) and DCM (50 mL) at 0° C. The mixture was stirred for 1 h, then the aqueous phase was extracted with DCM (3×50 mL). The organic phases were washed with sat'd aq. sodium bicarbonate (1×50 mL), water (1×50 mL), and brine (1×50 mL), then dried over MgSO4, filtered, and concentrated to afford the chloride 26B (64 mg, 79%).

Step C:

EXAMPLE 26

The compound of Example 26 can be prepared as described in Example 1, Step 6, by coupling the oxadiazolyl compound 5 of Example 1, Step 4, with the above chloropyrrolotriazine.

EXAMPLES 27-46

Compounds having the structure

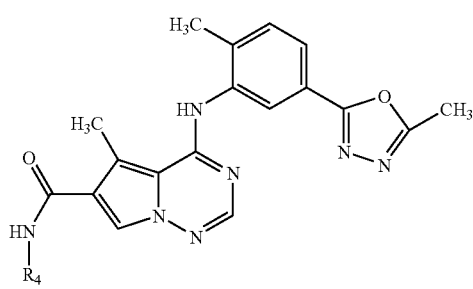

can be prepared according to the procedure described for Example 1 using the appropriate amine in place of n-propylamine in step H.

| Ex. # | R4 |
|---|---|
| 27 | 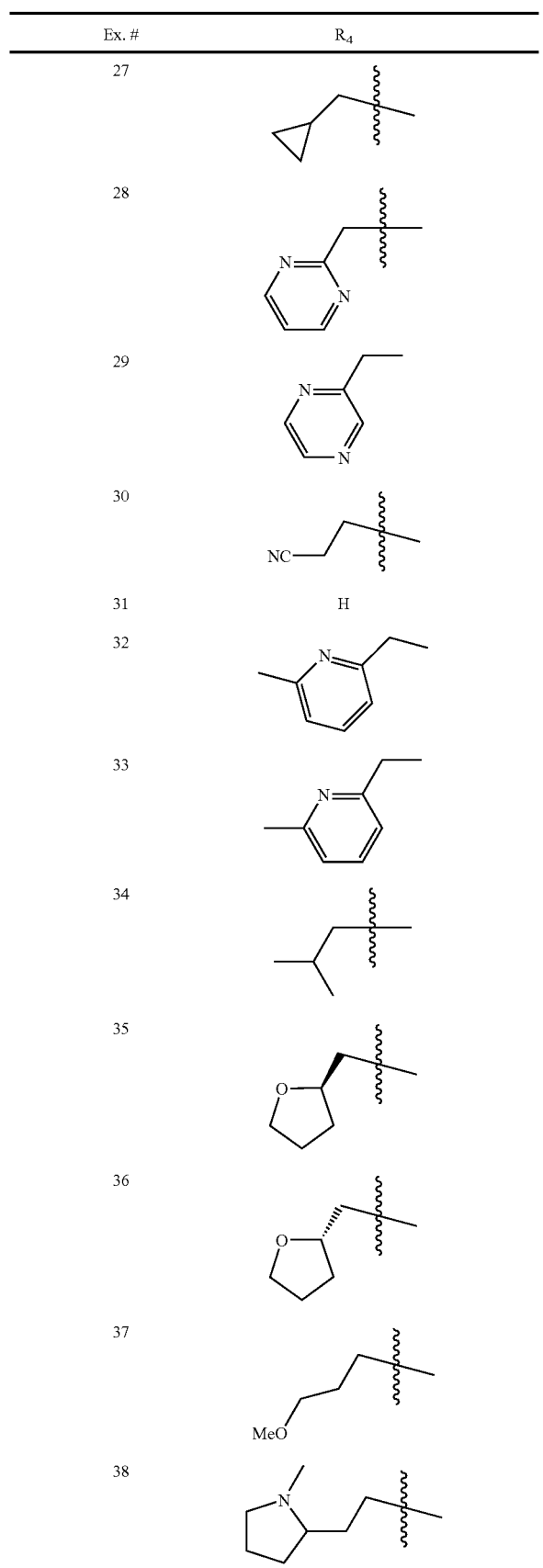 |
| 28 | |
| 29 | |
| 30 | |
| 31 | H |
| 32 | |
| 33 | |
| 34 | |
| 35 | |
| 36 | |
| 37 | |
| 38 | |
-continued
| Ex. # | R4 |
|---|---|
| 39 | 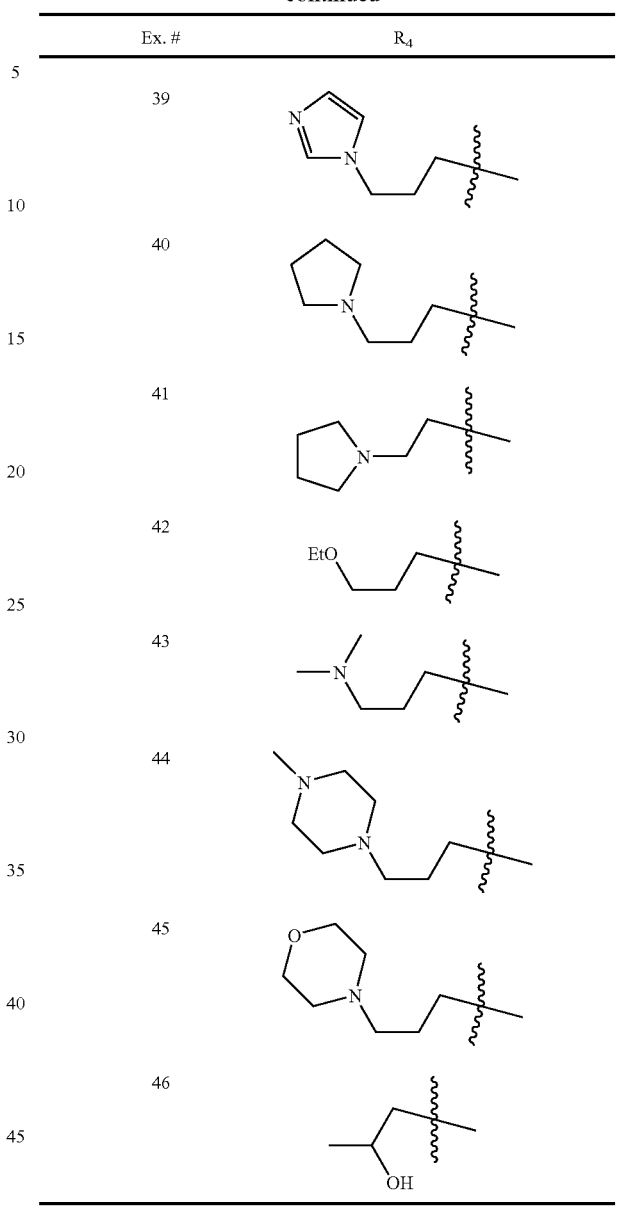 |
| 40 | |
| 41 | |
| 42 | |
| 43 | |
| 44 | |
| 45 | |
| 46 | |
EXAMPLE 47
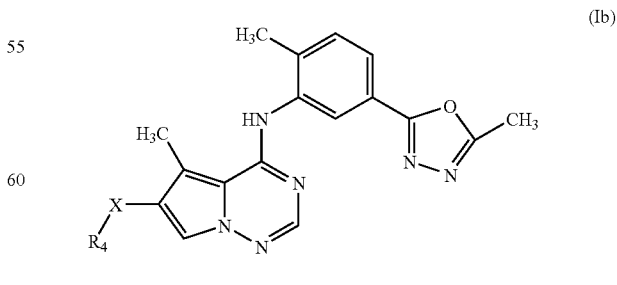
Compounds having the above formula (Ib), wherein the groups X—R4 are selected from the corresponding X—R4 groups described in U.S. patent application Ser. No. 10/420, 399 (incorporated herein by reference), can be prepared as described in Example 1, above, by coupling the chloropyrrolotriazine having the desired groups X—R$_4$, with the oxadiazolyl intermediate described in Example 1, Step D.

EXAMPLE 48

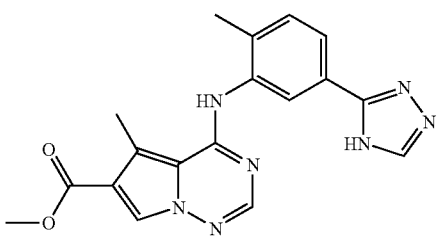

Step A:

2-Methyl-5-(4H-[1,2,4]triazol-3-yl)-phenylamine

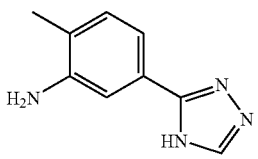

(48A)

Hydrogen chloride was bubbled through a solution of 3-nitro-p-tolunitrile (0.49 g, 3 mmol) in 40 mL of EtOH at room temp for 10 min. The solution was stirred at room temp for 60 min, and the solvent was then evaporated under vacuum to dryness to give a white solid.

The intermediate so obtained was dissolved in 20 mL of EtOH, neutralized with sodium ethoxide solution, and the resulting precipitate was removed by filtration. To the filtrate at rt. was added formic hydrazide (0.2 g, 3 mmol), stirring of the solution was then continued at room temp for 2 h, then the solvent was evaporated under vacuum. The residue was dissolved in 30 mL of m-xylene and refluxed at 150° C. for 16 h. The solvent was then evaporated under vacuum and the crude product was purified by flash chromatography to afford 0.26 g of nitro intermediate. (Yield: 43%). MS (m/z) calcd for $C_9H_8N_4O_2$ (MH+) 205.2, found, 205.1.

The nitro intermediate (190 mg) was dissolved in MeOH (5 mL) and Pd/C (10%, 75 mg) was added to the solution. A three-way adapter was attached to the flask and the reaction was evacuated with low vacuum then flushed with hydrogen gas several times. The reaction was left under 1 ATM of hydrogen for 1.5 h. The mixture was filtered through a pad of silica gel and evaporated to afford 2-methyl-5-(4H-[1,2,4] triazol-3-yl)-phenylamine (48A) along with a minor amount of over reduced material (61.5 mg). The crude material was used directly for further reaction.

Step B:

EXAMPLE 48

To a solution of the crude compound 48A (61.5 mg) in DMF (2 mL) was added 4-chloro-5-methyl-pyrrolo[2,1-f][1,2,4]triazine-6-carboxylic acid methyl ester (80 mg). The solution was heated to 55° C. for 1.5 hr, cooled to rt. and purified by reverse phase preparative HPLC to afford Example 48, above (34.1 mg, TFA salt) as a white solid. HPLC ret. t. (min): 2.72, MW: 363.4, LCMS[M+H]$^+$=364.

EXAMPLE 49

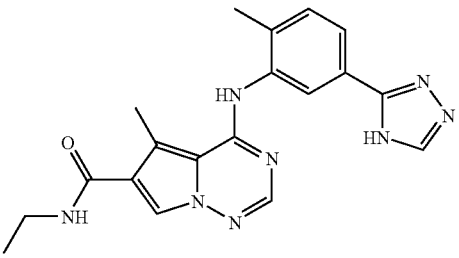

A solution of Example 48 (32 mg) and NaOH (1 N, 0.30 mL) in THF (0.3 mL) was heated to 55° C. overnight. The reaction was cooled and the THF evaporated. The solution was acidified to pH ~3 with 1N HCL and the resulting precipitate was collected by filtration to give a white solid (23.0 mg). This solid (11.5 mg) was dissolved in DMF (0.5 mL), along with EDCI (9.5 mg) and HOBt (7 mg) and the solution was stirred at rt. for 30 min. To this solution was added ethylamine-hydrochloride (6 mg) and DIPEA (0.011 mL) and the reaction was stirred at rt. The reaction was quenched with water and extracted with EtOAc. The extracts were washed with water and brine, dried over MgSO$_4$, and concentrated to give Example 49 as a white solid (6.5 mg) HPLC ret. t. (min): 2.08, MW: 376.4, LCMS[M+H]$^+$=377.

EXAMPLE 50

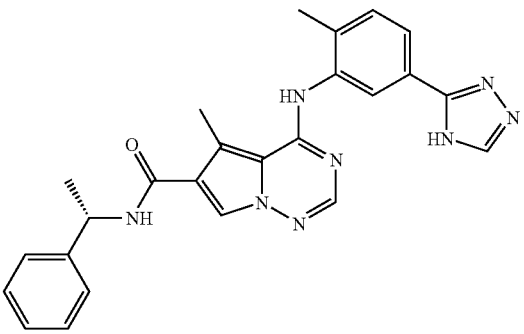

Example 50 was prepared in the same manner as described above for Example 49. Purified by reverse phase preparative HPLC to give a white solid (11.3 mg) HPLC ret. t. (min): 2.82, MW: 452.2, LCMS[M+H]$^+$=453.

EXAMPLE 51

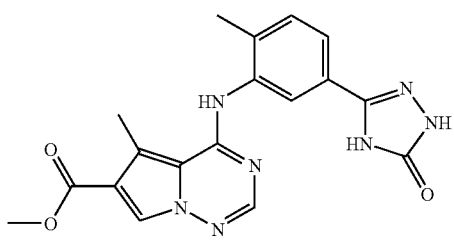

To a solution of 3-amino-4-methyl-benzoic acid ethyl ester (10 g) in EtOH (25 mL) was added anhydrous hydrazine (20 mL) dropwise over 45 min at rt. The reaction was stirred at rt. overnight, then concentrated to afford 3-amino-4-methyl-benzoic acid hydrazide (10 g) as a yellow solid. The hydrazide (500 mg) was dissolved in THF (5 mL) and TMS-isocycanate (0.41 mL) was added. After 2-3 h, HPLC analysis indicated 50-60% conversion of the hydrazide. No further conversion was found after 3 days at rt. Evaporation of the THF was followed by addition of 1 N NaOH (2 mL) and the solution was heated to 100° C. overnight. LCMS analysis indicated the desired oxo-triazole to be present along with the carboxylic acid corresponding to hydrolysis of the hydrazide. The solution was neutralized with 1N HCl and the crude product collected by filtration. The crude 5-(3-amino-4-methyl-phenyl)-2,4-dihydro-[1,2,4]triazol-3-one (100 mg) was dissolved in DMF (1 mL) along with 4-chloro-5-methyl-pyrrolo[2,1-f][1,2,4]triazine-6-carboxylic acid methyl ester (119 mg), and the solution was heated to 55° C. overnight. The product was purified by reverse phase preparative HPLC to afford Example 51 as a white solid (151 mg, TFA, hydrate), HPLC ret. t. (min): 2.33, MW: 379.4, LCMS[M+H$_2$O+H]$^+$=398.

EXAMPLE 52

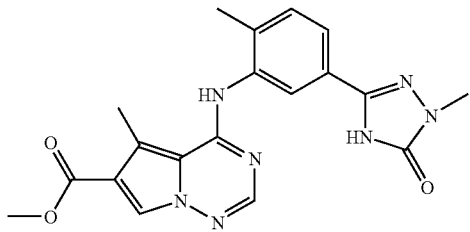

The above Example 52 was prepared following the same method as described above for Example 51, substituting methylisocyanate for TMSisocyanate. White solid (152 mg, TFA, hydrate) HPLC ret. t. (min): 2.41, MW: 393.4, LCMS [M+H$_2$O+H]$^+$=412.

EXAMPLE 53

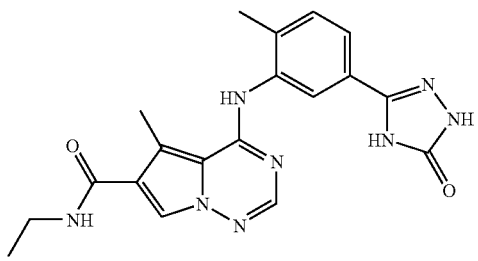

A solution of Example 51 (145 mg) in 1N NaOH (1.35 mL) and THF (1.35 mL) was heated to 55° C. for 8-9 h. The THF was evaporated and the solution acidified with 1N HCl to pH ~3. The resulting solid was collected by filtration and used directly for further reaction. This solid was dissolved in DMF (0.5 mL) along with EDCI (86 mg) and HOBt (61 mg), and the solution stirred at rt. for 30 min. The solution was divided into three equal parts. To one part of this solution was added ethylamine-hydrochloride (16 mg) and DIPEA (0.035 mL) and the reaction was stirred at rt. for several days. The reaction was quenched with water and layered with EtOAc. The resulting precipitate was collected by filtration to afford Example 53 as a white solid (13.3 mg) HPLC ret. t. (min): 1.66, MW: 392.4, LCMS[M+H]$^+$=393.

EXAMPLE 54

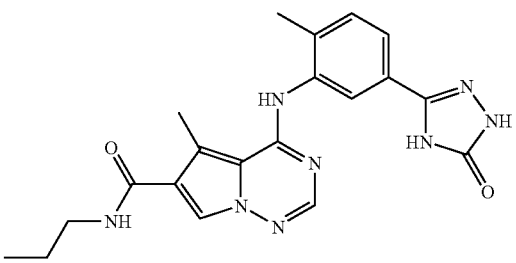

The above Example 54 was prepared following the same method as described above for Example 53. White solid (9.6 mg) HPLC ret. t. (min): 1.95, MW: 406.4, LCMS[M+H]$^+$=407.

EXAMPLE 55

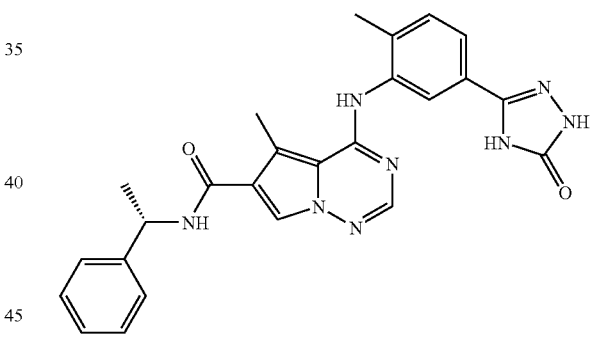

The above Example 55 was prepared following the same method as described above for Example 53. The initial precipitate was further purified by acetonitrile slurry. White solid (15 mg) HPLC ret. t. (min): 2.52, MW: 468.5, LCMS[M+H]$^+$=469.

EXAMPLE 56

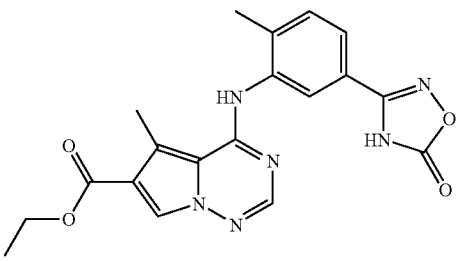

A solution of 4-(5-cyano-2-methyl-phenylamino)-5-methyl-pyrrolo[2,1-f][1,2,4]triazine-6-carboxylic acid ethyl ester, hydroxylamine hydrochloride (52 mg), and DIPEA (0.078 mL) in EtOH (5 mL) was stirred at 60° C. for 16 h. After cooling to rt., a precipitate was collected by filtration and washed with minimal EtOH to give a white solid (81.4 mg) that was used directly for subsequent reaction. The solid was stirred in THF (2 mL) along with carbonyldiimidazole (16.5 mg) at 60° C. for 3 days. Upon cooling to rt., a white solid formed and was collected by filtration to give Example 56 (15 mg). HPLC ret. t. (min): 3.36, MW: 394.4, LCMS[M+H]$^+$=395. The starting material to this reaction, 4-(5-cyano-2-methyl-phenylamino)-5-methyl-pyrrolo [2,1-f][1,2,4]triazine-6-carboxylic acid ethyl ester, hydroxylamine hydrochloride, can be prepared as described in Example 1, step F, by coupling the appropriate cyano-phenylamine with the chloropyrrolotriazine 1E.

What is claimed is:

1. A compound having the formula (I)

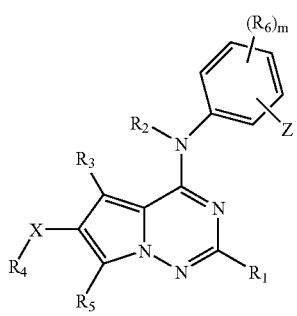

(I)

or an enantiomer, diastereomer, or pharmaceutically-acceptable salt thereof, wherein:

X is selected from —O—, —OC(=O)—, —S—, —S(=O)—, —SO$_2$—, —C(=O)—, —CO$_2$—, —NR$_8$—, —NR$_8$C(=O)—, —NR$_8$C(=O)NR$_9$—, —NR$_8$CO$_2$—, —NR$_8$SO$_2$—, —NR$_8$SO$_2$NR$_9$—, —SO$_2$NR$_8$—, —C(=O)NR$_8$—, halogen, nitro, and cyano, or X is absent;

Z is optionally-substituted heteroaryl;

R$_1$ and R$_5$ are independently selected from hydrogen, alkyl, substituted alkyl, —OR$_{14}$, —SR$_{14}$, —OC(=O)R$_{14}$, —CO$_2$R$_{14}$, —C(=O)NR$_{14}$R$_{14a}$, —NR$_{14}$R$_{14a}$, —S(=O)R$_{14}$, —SO$_2$R$_{14}$, —SO$_2$NR$_{14}$R$_{14a}$, —NR$_{14}$SO$_2$NR$_{14a}$R$_{14b}$, —NR$_{14a}$SO$_2$R$_{14}$, —NR$_{14}$C(=O)R$_{14a}$, —NR$_{14}$CO$_2$R$_{14a}$, —NR$_{14}$C(=O)NR$_{14a}$R$_{14b}$, halogen, nitro, and cyano;

R$_2$ is hydrogen or C$_{1-4}$alkyl;

R$_3$ is hydrogen, methyl, perfluoromethyl, methoxy, halogen, cyano, NH$_2$, or NH(CH$_3$);

R$_4$ is selected from:
(a) hydrogen, provided that R$_4$ is not hydrogen if X is —S(=O)—, —SO$_2$—, —NR$_8$CO$_2$—, or —NR$_8$SO$_2$—;
(b) alkyl, alkenyl, and alkynyl optionally independently substituted with keto and/or one to four R$_{17}$;
(c) aryl and heteroaryl either of which may be optionally independently substituted with one to three R$_{16}$; and
(d) heterocyclo and cycloalkyl either of which may be optionally independently substituted with keto and/or one to three R$_{16}$; or
(e) R$_4$ is absent if X is halogen, nitro, or cyano;

R$_6$ is attached to any available carbon atom of the phenyl ring and at each occurrence is independently selected from alkyl, halogen, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkylsulfonyl, sulfonamido, phenyl, benzyl, aryloxy, and benzyloxy, wherein each R$_6$ group in turn may be further substituted by one to two R$_{18}$;

R$_8$, R$_9$, R$_{14}$, R$_{14a}$ and R$_{14b}$ are independently selected from hydrogen, alkyl, substituted alkyl, aryl, cycloalkyl, heterocyclo, and heteroaryl, except when R$_{14}$ is joined to a sulphonyl group as in —S(=O)R$_{14}$, —SO$_2$R$_{14}$, and —NR$_{14a}$SO$_2$R$_{14}$, then R$_{14}$ is not hydrogen;

R$_{16}$ is selected from alkyl, R$_{17}$, and C$_{1-4}$alkyl substituted with keto (=O) and/or one to three R$_{17}$;

R$_{17}$ is selected from
(a) halogen, haloalkyl, haloalkoxy, nitro, cyano, —SR$_{23}$, —OR$_{23}$, —NR$_{23}$R$_{24}$, —NR$_{23}$SO$_2$R$_{25}$, —SO$_2$R$_{25}$, —SO$_2$NR$_{23}$R$_{24}$, —CO$_2$R$_{23}$, —C(=O)R$_{23}$, —C(=O)NR$_{23}$R$_{24}$, —OC(=O)R$_{23}$, —OC(=O)NR$_{23}$R$_{24}$, —NR$_{23}$C(=O)R$_{24}$, —NR$_{23}$CO$_2$R$_{24}$;
(b) aryl or heteroaryl either of which may be optionally substituted with one to three R$_{26}$; or
(c) cycloalkyl or heterocyclo optionally substituted with keto(=O) and/or one to three R$_{26}$;

R$_{18}$ and R$_{26}$ are independently selected from C$_{1-6}$alkyl, C$_{2-6}$alkenyl, halogen, haloalkyl, haloalkoxy, cyano, nitro, amino, C$_{1-4}$alkylamino, aminoC$_{1-4}$alkyl, hydroxy, hydroxyC$_{1-4}$alkyl, C$_{1-4}$alkoxy, C$_{1-4}$alkylthio, phenyl, five to six membered heterocyclo, (phenyl)C$_{1-4}$alkyl, phenoxy, and (phenyl)C$_{1-4}$alkoxy;

R$_{23}$ and R$_{24}$ are each independently selected from hydrogen, alkyl, alkenyl, substituted alkyl, substituted alkenyl, aryl, cycloalkyl, heteroaryl, and heterocyclo;

R$_{25}$ is selected from alkyl, substituted alkyl, aryl, heteroaryl, cycloalkyl and heterocyclo; and m is 0, 1, 2 or 3.

2. A compound of claim 1 having the formula (I*):

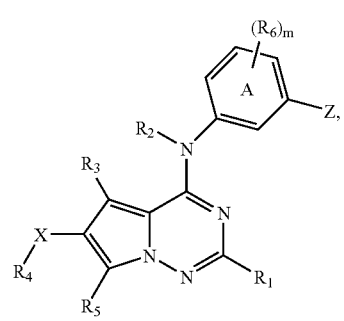

(I*)

or a pharmaceutically-acceptable salt thereof, in which Z is an optionally-substituted, monocyclic five-membered heteroaryl.

3. A compound according to claim 1, or a pharmaceutically-acceptable salt thereof, in which Z is selected from one of:

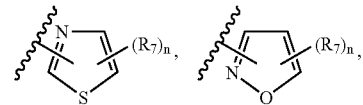

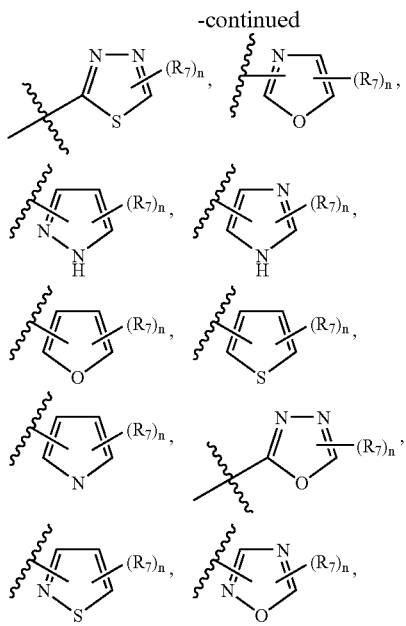

and

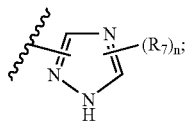

wherein, n is 0, 1, or 2; and

R₇ is selected from hydrogen, C₁₋₄alkyl, substituted C₁₋₄alkyl, trifluoromethyl, trifluoromethoxy, halogen, cyano, amino, —NH(C₁₋₄alkyl), N(C₁₋₄alkyl)₂, hydroxy, C₄alkoxy, thiol, alkylthio, phenyl, benzyl, phenyloxy, benzyloxy, C₃₋₇cycloalkyl, five-membered heteroaryl, and five to six membered heterocyclo; or as valence permits, R₇ may be taken together with one of two bonds forming a double bond of ring Z to form a keto (═O) group, or two R₇ groups attached to adjacent carbon atoms or an adjacent carbon and nitrogen atom may join to form a fused heterocyclo or carbocyclic ring, said fused ring in turn being optionally substituted with one to two of C₁₋₄alkyl, trifluoromethyl, trifluoromethoxy, halogen, cyano, amino, C₁₋₄alkylalmino, hydroxy, C₁₋₄alkoxy, phenyl, benzyl, phenyloxy, and benzyloxy.

4. A compound according to claim 3, or a pharmaceutically-acceptable salt thereof, in which Z is one of:

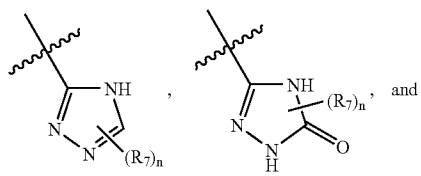

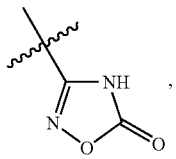

wherein R₇ is lower alkyl and n is 0 or 1.

5. A compound of claim 2, or a pharmaceutically-acceptable salt thereof, wherein:

Z is a 1,3,4 oxadiazol-2-yl optionally substituted at the 5 position with a group selected from R₇ₐ; and R₇ₐ is selected from C₁₋₄alkyl, substituted C₁₋₄alkyl, hydroxy, alkoxy, thiol, alkylthio, halogen, cyano, trifluoromethyl, trifluoromethoxy, amino, —NH(C₁₋₄alkyl), and N(C₁₋₄alkyl)₂.

6. A compound according to claim 2, or a pharmaceutically-acceptable salt thereof, wherein:

X is selected from —O—, —OC(═O)—, —NR₈C(═O)—, and —C(═O)NR₈—;

R₁ and R₅ are independently selected from hydrogen, alkyl, and substituted alkyl;

R₃ is hydrogen, methyl, perfluoromethyl, methoxy, halogen, cyano, NH₂, or NH(CH₃);

R₆ is attached to any available carbon atom of phenyl ring and at each occurrence is independently selected from C₁₋₄alkyl, halogen, trifluoromethoxy, trifluoromethyl, hydroxy, C₁₋₄alkoxy, thiol, C₁₋₄alkylthio, nitro, cyano, carboxy, and carboxyC₁₋₄alkyl; and m is 0, 1, or 2.

7. A compound according to claim 6, or a pharmaceutically-acceptable salt thereof, wherein:

R₁, R₂ and R₅ are each hydrogen;

R₃ is methyl, —CF₃, or —OCF₃;

R₈ and R₉ are selected from hydrogen and C₁₋₄alkyl; and

R₆ is attached to the phenyl ring at the 2 and/or 6 positions and is selected from C₁₋₆alkyl, trifluoromethoxy, trifluoromethyl, and cyano; and m is 1 or 2.

8. A compound according to claim 2, or a pharmaceutically-acceptable salt thereof, wherein:

R₁, R₂ and R₅ are each hydrogen;

R₃ is methyl;

Z is 1,3,4-oxadiazol-2-yl or triazol-5-yl, each of Z optionally substituted with up to one of methyl or ethyl;

X is —C(═O)— or —C(═O)—NH—; when X is —C(═O)—, then R₄ is phenyl or pyridyl optionally substituted with up to two R₁₆; and when X is —C(═O)NH—, R₄ is straight or branched C₂₋₆alkyl or optionally-substituted benzyl;

R₆ is attached to phenyl ring at the 2 position and is methyl, ethyl, halogen, trifluoromethoxy, trifluoromethyl, hydroxy, methoxy, ethoxy, or cyano;

R₁₆ is selected from C₁₋₄alkyl, halogen, hydroxy, C₁₋₄alkoxy, trifluoromethyl, trifluoromethoxy, cyano, nitro, phenyl, benzyl, phenyloxy, benzyloxy, NH₂, NH(C₁₋₄alkyl), N(C₁₋₄alkyl)₂ and/or a C₁₋₄alkyl substituted with one to two of halogen, hydroxy, C₁₋₄alkoxy, trifluoromethyl, trifluoromethoxy, cyano, nitro, phenyl, benzyl, phenyloxy, benzyloxy, NH₂, NH(C₁₋₄alkyl), and/or N(C₁₋₄alkyl)₂; and m is 1.

9. A compound according to claim 1 or a pharmaceutically acceptable salt thereof, in which R₁ is hydrogen.

10. A compound according to claim 1, or a pharmaceutically acceptable salt thereof, in which $R_2$ is hydrogen.

11. A compound according to claim 1, or a pharmaceutically-acceptable salt thereof, wherein:

$R_3$ is methyl, —$CF_3$, or —$OCF_3$.

12. A compound according to claim 1, or a pharmaceutically-acceptable salt thereof, wherein:

X is —C(═O)— or —C(═O)NH—.

13. A compound according to claim 1, or a pharmaceutically acceptable salt thereof, in which X is —C(═O)NH— and $R_4$ is $C_{2-6}$ alkyl, optionally-substituted benzyl, or a heterocyclic or heteroaryl ring selected from diazepinyl, morpholinyl, piperidinyl, and pyrrolidinyl, said heterocycle being optionally substituted with one to two of $C_{1-4}$alkyl, hydroxy, $C_{1-4}$alkoxy, phenyl, and/or benzyl.

14. A compound according to claim 1, or a pharmaceutically acceptable salt thereof, in which X is —C(═O)— and $R_4$ is phenyl, pyridyl, pyrimidinyl, or pyrazinyl optionally-substituted with one to two of $C_{1-4}$alkyl, halogen, hydroxy, $C_{1-4}$alkoxy, trifluoromethyl, trifluoromethoxy, cyano, nitro, phenyl, benzyl, phenyloxy, benzyloxy, $NH_2$, $NH(C_{1-4}$alkyl), $N(C_{1-4}$alkyl$)_2$ and/or a $C_{1-4}$alkyl substituted with one to two of halogen, hydroxy, $C_{1-4}$alkoxy, trifluoromethyl, trifluoromethoxy, cyano, nitro, phenyl, benzyl, phenyloxy, benzyloxy, $NH_2$, $NH(C_{1-4}$alkyl), and/or $N(C_{1-4}$alkyl$)_2$.

15. A compound according to claim 1 or a pharmaceutically acceptable salt thereof, in $R_5$ is hydrogen or $CH_3$.

16. A compound having the formula,

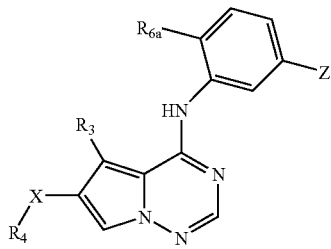

or an enantiomer, diastereomer, or a pharmaceutically acceptable salt thereof, wherein:

$R_3$ is methyl or $CF_3$;
X is —C(═O)— or —C(═O)NH—;
Z is selected from one of

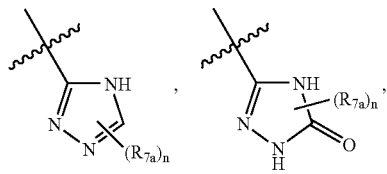

-continued

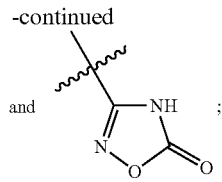

$R_4$ is straight or branched $C_{2-6}$alkyl; cycloalkyl optionally substituted with keto and/or up to two $R_{16}$; heterocycle or heteroaryl optionally substituted with keto and/or up to two $R_{16}$; $C_{1-4}$alkyl substituted with up to three of halogen, trifluoromethyl, cyano, hydroxy, alkoxy, haloalkyl, haloalkoxy, nitro, phenyl, phenyloxy or benzyloxy, wherein said phenyl group is optionally substituted with one to two $R_{16}$; or phenyl optionally substituted with zero to two $R_{16}$;

$R_{6a}$ is selected from lower alkyl, halogen, trifluoromethoxy, trifluoromethyl, hydroxy, $C_{1-4}$alkoxy, nitro, amino, $C_{1-4}$alkylamino, and cyano;

$R_{7a}$ is lower alkyl; and $R_{16}$ is selected from $C_{1-4}$alkyl, halogen, hydroxy, $C_{1-4}$alkoxy, trifluoromethyl, trifluoromethoxy, cyano, nitro, phenyl, benzyl, phenyloxy, benzyloxy, $NH_2$, $NH(C_{1-4}$alkyl), $N(C_{1-4}$alkyl$)_2$ and/or a $C_{1-4}$alkyl substituted with one to two of halogen, hydroxy, $C_{1-4}$alkoxy, trifluoromethyl, trifluoromethoxy, cyano, nitro, phenyl, benzyl, phenyloxy, benzyloxy, $NH_2$, $NH(C_{1-4}$alkyl), and/or $N(C_{1-4}$alkyl$)_2$;

n is 0 or 1.

17. A pharmaceutical composition comprising at least one compounds according to claim 1 and a pharmaceutically-acceptable carrier or diluent.

18. A pharmaceutical composition at least one or more compound according to claim 16 and a pharmaceutically-acceptable carrier or diluent.

19. A method of treating asthma, adult respiratory distress syndrome, chronic obstructive pulmonary disease, chronic pulmonary inflammatory disease, inflammatory bowel disease, osteoporosis, psoriasis, graft vs. host rejection, atherosclerosis, multiple myeloma, myocardial ischemia, rheumatoid arthritis, psoriatic arthritis, traumatic arthritis, rubella arthritis, goaty arthritis, and osteoarthritis, comprising administering to a patient in need of such treatment a pharmaceutical composition according to claim 17.

20. A method of treating asthma, adult respiratory distress syndrome, chronic obstructive pulmonary disease, chronic pulmonary inflammatory disease, inflammatory bowel disease, osteoporosis, psoriasis, graft vs. host rejection, atherosclerosis, multiple myeloma, myocardial ischemia, rheumatoid arthritis, psoriatic arthritis traumatic arthritis, rubella arthritis gouty arthritis and osteoarthritis, comprising administering to a patient in need of such treatment a pharmaceutical composition according to claim 18.

* * * * *

UNITED STATES PATENT AND TRADEMARK OFFICE
CERTIFICATE OF CORRECTION

PATENT NO. : 7,388,009 B2  
APPLICATION NO. : 10/678388  
DATED : June 17, 2008  
INVENTOR(S) : Katerina Leftheris et al.

Page 1 of 2

It is certified that error appears in the above-identified patent and that said Letters Patent is hereby corrected as shown below:

On the Title Page:

Item (56) References Cited, under OTHER PUBLICATIONS,

Banker, G.S. et al. reference, change "Pharmaceutices" to -- Pharmaceutics --.

The reference should read:

-- Banker, G.S. et al., "Modern Pharmaceutics", 3ed.", Marcel Dekker, New York, 1996, pp. 451 and 596.* --.

Johansen, C. et al., The Journal of Immunology reference, change "Posttrancriptional" to -- Posttranscriptional --.

The reference should read:

-- Johansen, C., et al., "Protein Expression of TNF-α in Psoriatic Skin Is Regulated at a Posttranscriptional Level by MAPK-Activated Protein Kinase $2^{1}$", The Journal of Immunology, vol. 176, pp. 1431-1438, (2006). --.

Kumar, S. et al. reference, change "Kinaes" to -- Kinases --.

The reference should read:

-- "Kumar, S., et al., "P38 MAP Kinases Key Signalling Molecules as Therapeutic Targets for Inflammatory Diseases", vol. 2, pp. 717-726, (2003). --.

In the Claims:

Claim 1:

Column 44, line 4, change "alkysulfonyl" to -- alkylsulfonyl --.

Signed and Sealed this  
First Day of March, 2011

David J. Kappos  
*Director of the United States Patent and Trademark Office*

CERTIFICATE OF CORRECTION (continued)
U.S. Pat. No. 7,388,009 B2

In the Claims:

Claim 2:

Column 44, lines 42 to 52, change

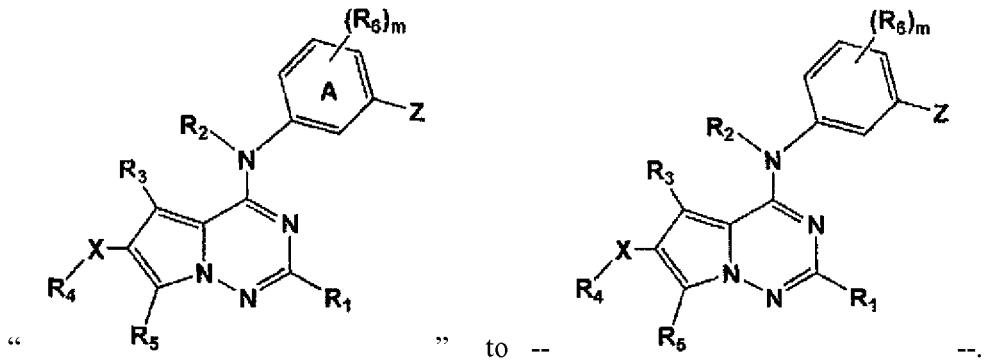

Claim 3:

Column 45, line 42, change "C₄alkoxy" to -- $C_{1-4}$alkoxy --.

Column 45, line 53, change "$C_{1-4}$alkylalmino" to -- $C_{1-4}$alkylamino --.

Claim 5:

Column 46, line 13, change "1,3,4 oxadiazolyl-2-yl" to -- 1,3,4-oxadiazolyl-2-yl --.

Claim 6:

Column 46, line 27, after "atom of", insert -- the --.

Claim 7:

Column 46, line 38, change "6" to -- 4 --.

Claim 8:

Column 46, line 47, after "Z", insert -- is --.

Column 46, line 54, after "attached to", insert -- the --.

Claim 15:

Column 47, line 29, after "in", insert -- which --.

Claim 17:

Column 48, line 32, after "one", insert -- or more --.

Claim 18:

Column 48, line 35, after "composition", insert -- comprising --.

Claim 19:

Column 48, line 45, change "goaty" to -- gouty --.

Claim 20:

Column 48, line 53, after "arthritis", insert -- , --.

Column 48, line 54, after "arthritis", insert -- , --.